United States Patent [19]

Culbertson et al.

[11] Patent Number: 5,081,254
[45] Date of Patent: Jan. 14, 1992

[54] ANTIBACTERIAL AGENTS

[75] Inventors: Townley P. Culbertson, Ann Arbor; John M. Domagala, Canton; Susan E. Hagen, Canton Township, Wayne County; Joseph P. Sanchez, Novi, all of Mich.

[73] Assignee: Warner-Lambert Company, Morris Plains, N.J.

[21] Appl. No.: 538,858

[22] Filed: Jun. 15, 1990

Related U.S. Application Data

[60] Continuation-in-part of Ser. No. 487,363, Mar. 1, 1990, abandoned, which is a division of Ser. No. 222,608, Jul. 25, 1988, Pat. No. 4,929,613, which is a continuation-in-part of Ser. No. 89,382, Aug. 26, 1987, abandoned.

[51] Int. Cl.$^5$ .................. C07D 211/52; C07D 211/32
[52] U.S. Cl. ..................................... 546/217; 546/235
[58] Field of Search ............................... 546/217, 235

[56] References Cited

U.S. PATENT DOCUMENTS 4,880,814  11/1989  Chu et al. ............................ 514/300

OTHER PUBLICATIONS

Broetell, H., "Syringe and Column Adsorption . . . ", CA 93:179062s (1980).

Primary Examiner—C. Warren Ivy
Assistant Examiner—Celia Chang
Attorney, Agent, or Firm—Elizabeth M. Anderson

[57] ABSTRACT

A novel series of quinoline-, naphthyridine- and benzoxazine-carboxylic acids useful as antibacterial agents is described. Novel methods for preparing the compounds as well as novel intermediates are also described as are methods for their formulation and the use thereof in treating bacterial infections.

7 Claims, No Drawings

ANTIBACTERIAL AGENTS

CROSS-REFERENCE TO RELATED APPLICATION

This is a continuation-in-part of U.S. application Ser. No. 487,363, filed Mar. 1, 1990, now abandoned which is a divisional of U.S. application Ser. No. 222,608, filed July 25, 1988 now U.S. Pat. No. 4,929,613, which is a continuation-in-part of U.S. application Ser. No. 089,382, filed Aug. 26, 1987, now abandoned.

BACKGROUND OF THE INVENTION

U.S. Pat. No. 4,623,650 discloses certain 6-fluoro-7-aryl-1,4-dihydroquinoline-3-carboxylic acids having the formula:

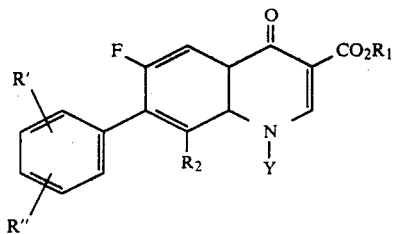

in which $R_1$ is hydrogen, 1-4 carbon alkyl, benzyl, or a cation; $R_2$ is hydrogen or fluorine; Y is 1-3 carbon alkyl, hydrogen, or poly haloalkyl, hydroxyethyl, cyclopropyl, vinyl, alkylphenyl, 4-hydroxyphenyl or 4-fluorophenyl; R' is hydrogen, 1-4 alkyl, sulphinyl, sulphonyl, hydroxy, 1-3 carbon hydroxyalkyl, aminoalkyl, $NH_2$, formamido, 2-3 carbon alkanoylamino, aminosulphonyl, $NO_2$, formyl, N-(N',N'-dimethylformamido); R" is hydrogen, 3-hydroxy or 3-chloro provided that R' and R" are not both hydrogen. Antibacterial activity is disclosed.

U.S. Pat. No. 3,472,859 discloses certain compounds having the formula:

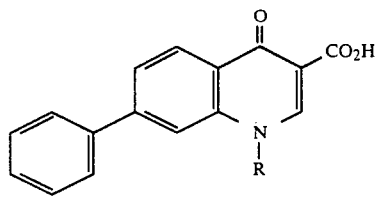

wherein R is lower alkyl. Fungistatic activity is disclosed.

U.S. Pat. No. 3,907,808 discloses certain 1,4-dihydro-1-(lower alkyl)-4-oxo-7-(4-pyridyl)-3-quinolinecarboxylic acids and esters of the formula:

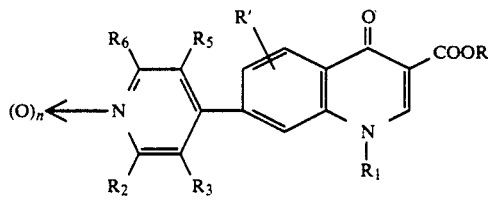

where R is hydrogen, lower alkyl or $CH_2OAc$ where Ac is lower alkanoyl or benzoyl; $R_1$ is lower alkyl, lower hydroxyalkyl or lower haloalkyl; R' is hydrogen, halogen, lower alkyl or lower alkoxy; n is 0 or 1; and $R_2$, $R_3$, $R_5$, and $R_6$ are each selected from hydrogen, lower alkyl, lower alkoxy, halogen, hydroxy, loweralkanoyloxy, hydroxymethyl, aminomethyl, lower alkanoylaminomethyl, amino, formyl, cyano, carbamyl, carboxy, and lower carbalkoxy. Antibacterial activity is disclosed.

European Publication 86 107840 discloses certain bridged quinolines of the formula:

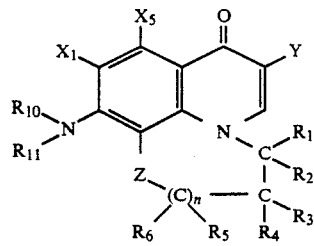

where Y is COOH, CN or $COOR_7$, or $CONR_8R_9$; $X_1$ is hydrogen, $NO_2$, 1-3 carbon alkyl or halogen; $X_5$ is hydrogen, halogen or methyl; $NR_{10}R_{11}$ is a 5 or 6 member heterocycle with optional substituents in the ring and on the ring; and Z is oxygen or $NR_{15}$. Antibacterial activity is disclosed.

SUMMARY OF THE INVENTION

One aspect of the present invention is a compound of formula I

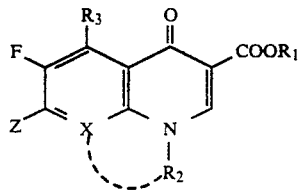

or a pharmaceutically acceptable acid addition salt thereof wherein:

$R_1$ is hydrogen, lower alkyl of from one to six carbon atoms, or a cation;

$R_2$ is alkyl, alkyl substituted by halogen, cycloalkyl, cycloalkyl substituted by hydroxy, alkyl or aryl, aryl substituted by alkyl, alkoxy, or halogen, heteroaryl, alkenyl, vinyl, $-OCH_3$, or $-NHCH_3$;

$R_3$ is hydrogen, halogen, $OR_4$, wherein $R_4$ is hydrogen or alkyl, $NHR_5$ wherein $R_5$ is hydrogen or lower alkyl, $CF_3$, or COOH;

X is CH, CF, CBr, CCl, N, $CNO_2$, $CNH_2$, $CCF_3$, or $COR_6$ wherein $R_6$ is hydrogen or alkyl;

X and $R_2$ when taken together may form a five or six member ring which may contain:

two or more carbons, one oxygen, one sulphur, one nitrogen or $NR_{15}$ wherein $R_{15}$ is hydrogen, alkyl, alkyl substituted by halogen, $CF_3$, $NO_2$, CN, OH, alkoxy of from one to three carbon atoms, alkythio of from one to three carbon atoms, aryloxy, arylthio or ester group with from one to three carbons in the alcohol residue, phenyl, phenyl substituted by halogen, $NO_2$, alkyl, alkoxy, or alkythio, $R_{16}CO$, $R_{17}SO_2$, $-CONR_{18}R_{19}$, or $SO_2NR_{20}R_{21}$ wherein $R_{16}$ and $R_{17}$ are alkyl, phenyl, or substituted phenyl, and $R_{18}$, $R_{19}$, $R_{20}$, and $R_{21}$ are each independently hydrogen, alkyl, phenyl or substituted phenyl;

Z is

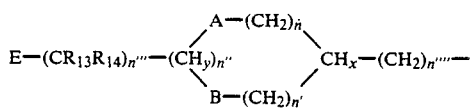  II wherein one endocyclic double bond may be present between any two consecutive ring positions or two alternating or nonalternating endocyclic double bonds may be present in the ring;

wherein n, n', n''', and n'''' are each independently 0, 1, or 2;

n'' is 0, 1, 2, or 3;

y is 1 or 2;

x is 0 or 1;

A and B are each independently CH, CH$_2$, NR$_7$ wherein R$_7$ is hydrogen, lower alkyl, or R$_7$ is R$_8$CO wherein R$_8$ is alkyl of from one to ten carbon atoms, arylalkyl, aryl wherein the aryl or alkyl may be substituted by hydroxy, halogen, COOH, or CONHR$_9$ wherein R$_9$ is hydrogen or alkyl of one to four carbon atoms; and when A is NR$_7$, B can be O or S or when B is NR$_7$, A can be absent;

(CR$_{13}$R$_{14}$)$_{n'''}$ wherein R$_{13}$ and R$_{14}$ are each independently hydrogen or lower alkyl; and E is hydrogen, alkyl, OR$_{10}$ wherein R$_{10}$ is hydrogen or alkyl, NR$_{11}$R$_{12}$ wherein R$_{11}$ and R$_{12}$ are each independently hydrogen, lower alkyl, cycloalkyl, alkylaryl, alkylheteroaryl, alkanoyl, amidine, peptide or urethane or R$_{11}$ and R$_{12}$ when taken together with the nitrogen to which they are attached form a ring of from three to six carbon atoms or

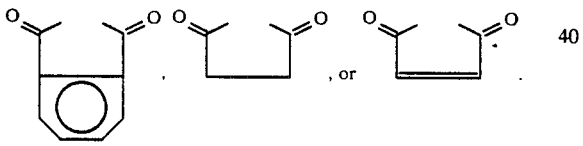

Preferred compounds of the invention are those wherein:

$R_1$ is hydrogen, alkyl, or a cation;

$R_2$ is alkyl, cycloalkyl, cycloalkyl substituted by hydroxy, aryl, substituted aryl, or vinyl;

$R_3$ is hydrogen, or NHR$_5$ wherein R$_5$ is hydrogen or lower alkyl;

X is CH, CF, CBr, CCl, N, CNO$_2$, or CNH$_2$;

X and R$_2$ when taken together form a 5 or 6 member ring which may contain one oxygen or one sulphur; and Z is as above.

Other preferred compounds of the invention are those wherein:

$R_1$ is hydrogen, alkyl of from one to three carbon atoms, or a pharmaceutically acceptable salt;

$R_2$ is alkyl of from one to three carbon atoms, cycloalkyl, vinyl, or 4-fluorophenyl;

$R_3$ is hydrogen or NH$_2$;

X is CH, CCl, CF, N, CNO$_2$ or CNH$_2$ or X and R$_2$ when taken together form a 5 or 6 member ring containing one oxygen; and Z is

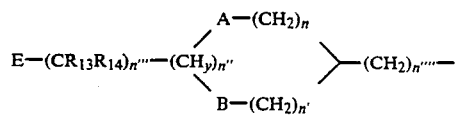  II wherein n and n' are each independently 0 or 1, n'''' is 0;

n''' is 0 or 1; and n'' is 1;

A and B are each CH$_2$ or NR$_7$; (CR$_{13}$R$_{14}$)$_{n'''}$ wherein R$_{13}$ and R$_{14}$ are each independently hydrogen or lower alkyl of from one to two carbon atoms; and E is hydrogen, —NR$_{11}$R$_{12}$ wherein R$_{11}$ and R$_{12}$ are each independently hydrogen, lower alkyl, or acyl.

Other preferred compounds of the invention are those wherein Z is

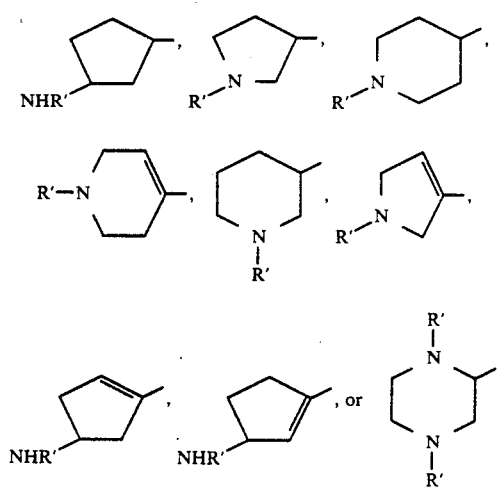

wherein R' is hydrogen, lower alkyl, and α-amino acid acyl.

Particularly preferred compounds of the invention are compounds having the names:

1-cyclopropyl-7-[3-(1,3-dihydro-1,3-dioxo-2H-indo2-lyl)cyclopentyl]-6-fluoro-1,4-dihydro-4-oxo-3-quinolinecarboxylic acid ethyl ester;

7-[3-(amino)cyclopentyl]-1-cyclopropyl-6-fluoro-1,4-dihydro-4-oxo-3-quinolinecarboxylic acid hydrochloride;

ethyl 1-cyclopropyl-6-fluoro-1,4-dihydro-7-(1-methyl-4-piperidinyl)-4-oxo-3-quinolinecarboxylate;

1-cyclopropyl-6-fluoro-1,4-dihydro-7-(1-methyl-4-piperidinyl)-4-oxo-3-quinolinecarboxylic acid;

7-[3-(amino)cyclopenten-1-yl]-1-cyclopropyl-6-fluoro-1,4-dihydro-4-oxo-3-quinolinecarboxylic acid;

7-[4-(amino)cyclopenten-1-yl]-1-cyclopropyl-6-fluoro-1,4-dihydro-4-oxo-3-quinolinecarboxylic acid;

7-[3-(amino)cyclopentyl]-1-cyclopropyl-6,8-difluoro-1,4-dihydro-4-oxo-3-quinolinecarboxylic acid;

7-[3-(ethylamino)cyclopentyl]-1-cyclopropyl-6-fluoro-1,4-dihydro-4-oxo-3-quinolinecarboxylic acid;

7-[3-(dimethylamino)cyclopentyl]-1-cyclopropyl-6-fluoro-1,4-dihydro-4-oxo-3-quinolinecarboxylic acid;

7-[3-(amino)cyclopentyl]-1-(4-fluorophenyl)-6-fluoro-1,4-dihydro-4-oxo-3-quinolinecarboxylic acid;

7-[3-(ethylamino)cyclopentyl]-1-(4-fluorophenyl)-6-fluoro-1,4-dihydro-4-oxo-3-quinolinecarboxylic acid;

7-[3-(dimethylamino)cyclopentyl]-1-(4-fluorophenyl)-6-fluoro-1,4-dihydro-4-oxo-3-quinolinecarboxylic acid;
8-amino-7-[3-(amino)cyclopentyl]-1-cyclopropyl-6-fluoro-1,4-dihydro-4-oxo-3-quinolinecarboxylic acid;
8-amino-7-[3-(ethylamino)cyclopentyl]-1-cyclopropyl-6-fluoro-1,4-dihydro-4-oxo-3-quinolinecarboxylic acid;
8-amino-7-[3-(dimethylamino)cyclopentyl]-1-cyclopropyl-6-fluoro-1,4-dihydro-4-oxo-3-quinolinecarboxylic acid;
8-amino-7-[3-(amino)cyclopentyl]-1-(4-fluorophenyl)-6-fluoro-1,4-dihydro-4-oxo-3-quinolinecarboxylic acid;
8-amino-7-[3-(ethylamino)cyclopentyl]-1-(4-fluorophenyl)-6-fluoro-1,4-dihydro-4-oxo-3-quinolinecarboxylic acid;
8-amino-7-[3-(dimethylamino)cyclopentyl]-1-(4-fluorophenyl)-6-fluoro-1,4-dihydro-4-oxo-3-quinoline carboxylic acid;
7-[3-(amino)cyclohexyl]-1-cyclopropyl-6-fluoro-1,4-dihydro-4-oxo-3-quinolinecarboxylic acid;
7-[3-(amino)cyclohexen-1-yl]-1-cyclopropyl-6-fluoro-1,4-dihydro-4-oxo-3-quinolinecarboxylic acid;
7-[4-(amino)cyclohexen-1-yl]-1-cyclopropyl-6-fluoro-1,4-dihydro-4-oxo-3-quinolinecarboxylic acid;
7-[3-(dimethylamino)cyclohexyl]-1-cyclopropyl-6-fluoro-1,4-dihydro-4-oxo-3-quinolinecarboxylic acid;
7-[3-(amino)cyclohexyl]-1-(4-fluorophenyl)-6-fluoro-1,4-dihydro-4-oxo-3-quinolinecarboxylic acid;
7-[3-(ethylamino)cyclohexyl]-1-(4-fluorophenyl)-6-fluoro-1,4-dihydro-4-oxo-3-quinolinecarboxylic acid;
7-[3-(dimethylamino)cyclohexyl]-1-(4-fluorophenyl)-6-fluoro-1,4-dihydro-4-oxo-3-quinolinecarboxylic acid;
8-amino-7-[3-(amino)cyclohexyl]-1-cyclopropyl-6-fluoro-1,4-dihydro-4-oxo-3-quinolinecarboxylic acid;
8-amino-7-[3-(ethylamino)cyclohexyl]-1-cyclopropyl-6-fluoro-1,4-dihydro-4-oxo-3-quinolinecarboxylic acid;
8-amino-7-[3-(dimethylamino)cyclohexyl]-1-cyclopropyl-6-fluoro-1,4-dihydro-4-oxo-3-quinolinecarboxylic acid;
8-amino-7-[3-(amino)cyclohexyl]-1-(4-fluorophenyl)-6-fluoro-1,4-dihydro-4-oxo-3-quinolinecarboxylic acid;
8-amino-7-[3-(ethylamino)cyclohexyl]-1-(4-fluorophenyl)-6-fluoro-1,4-dihydro-4-oxo-3-quinolinecarboxylic acid;
8-amino-7-[3-(dimethylamino)cyclohexyl]-1-(4-fluorophenyl)-6-fluoro-1,4-dihydro-4-oxo-3-quinolinecarboxylic acid;
1-cyclopropyl-6-fluoro-1,4-dihydro-7-(4-piperidinyl)-4-oxo-3-quinolinecarboxylic acid;
1-cyclopropyl-6-fluoro-1,4-dihydro-7-(1-methyl-4-piperidinyl)-4-oxo-3-quinolinecarboxylic acid;
6-fluoro-1-(4-fluorophenyl)-1,4-dihydro-7-(4-piperidinyl)-4-oxo-3-quinolinecarboxylic acid;
6-fluoro-1-(4-fluorophenyl)-1,4-dihydro-7-(1-methyl-4-piperidinyl)-4-oxo-3-quinolinecarboxylic acid;
8-amino-1-cyclopropyl-6-fluoro-1,4-dihydro-7-(4-piperidinyl)-4-oxo-3-quinolinecarboxylic acid;
8-amino-1-cyclopropyl-6-fluoro-1,4-dihydro-7-(1-methyl-4-piperidinyl)-4-oxo-3-quinolinecarboxylic acid;
8-amino-6-fluoro-1-(4-fluorophenyl)-1,4-dihydro-7-(4-piperidinyl)-4-oxo-3-quinolinecarboxylic acid;
8-amino-6-fluoro-1-(4-fluorophenyl)-1,4-dihydro-7-(1-methyl-4-piperidinyl)-4-oxo-3-quinolinecarboxylic acid;
1-cyclopropyl-6-fluoro TM 1,4-dihydro-7-(3-piperidinyl)-4-oxo-3-quinolinecarboxylic acid;
1-cyclopropyl-6-fluoro-1,4-dihydro-7-(1-methyl-3-piperidinyl)-4-oxo-3-quinolinecarboxylic acid;
6-fluoro-1-(4-fluorophenyl)-1,4-dihydro-7-(3-piperidinyl)-4-oxo-3-quinolinecarboxylic acid;
6-fluoro-1-(4-fluorophenyl)-1,4-dihydro-7-(1-methyl-3-piperidinyl)-4-oxo-3-quinolinecarboxylic acid;
8-amino-1-cyclopropyl TM 6-fluoro-1,4-dihydro-7-(3-piperidinyl)-4-oxo-3-quinolinecarboxylic acid;
8-amino-1-cyclopropyl-6-fluoro-1,4-dihydro-7-(1-methyl-3-piperidinyl)-4-oxo-3-quinolinecarboxylic acid;
8-amino-6-fluoro-1-(4-fluorophenyl)-1,4-dihydro-7-(3-piperidinyl)-4-oxo-3-quinolinecarboxylic acid;
8-amino-6-fluoro-1-(4-fluorophenyl)-1,4-dihydro-7-(1-methyl-3-piperidinyl)-4-oxo-3-quinolinecarboxylic acid;
1-cyclopropyl-6-fluoro-1,4-dihydro-7-(3-pyrrolidinyl)-4-oxo-3-quinolinecarboxylic acid;
1-cyclopropyl-6-fluoro-1,4-dihydro-7-(1-methyl-3-pyrrolidinyl)-4-oxo-3-quinolinecarboxylic acid;
6-fluoro-1-(4-fluorophenyl)-1,4-dihydro-7-(3-pyrrolidinyl)-4-oxo-3-quinolinecarboxylic acid;
6-fluoro-1-(4-fluorophenyl)-1,4-dihydro-7-(1-methyl-3-pyrrolidinyl)-4-oxo-3-quinolinecarboxylic acid;
6-fluoro-1-(4-fluorophenyl)-1,4-dihydro-7-(3-pyrrolidinyl)-4-oxo-3-quinolinecarboxylic acid;
6-fluoro-1-(4-fluorophenyl)-1,4-dihydro-7-(1-methyl-3-pyrrolidinyl)-4-oxo-3-quinolinecarboxylic acid;
8-amino-1-cyclopropyl-6-fluoro-1,4-dihydro-7-(3-pyrrolidinyl)-4-oxo-3-quinolinecarboxylic acid;
8-amino-1-cyclopropyl-6-fluoro-1,4-dihydro-7-(1-methyl-3-pyrrolidinyl)-4-oxo-3-quinolinecarboxylic acid;
8-amino-6-fluoro-1-(4-fluorophenyl)-1,4-dihydro-7-(3-pyrrolidinyl)-4-oxo-3-quinolinecarboxylic acid;
8-amino-6-fluoro-1-(4-fluorophenyl)-1,4-dihydro-7-(1-methyl-3-pyrrolidinyl)-4-oxo-3-quinolinecarboxylic acid;
1-cyclopropyl-6-fluoro-1,4-dihydro-4-oxo-7-(2-piperazinyl)-3-quinolinecarboxylic acid, and
1-cyclopropyl-6-fluoro-1,4-dihydro-4-oxo-7-(1,2,3,6-tetrahydro-4-pyridyl)-3-quinolinecarboxylic acid.

The invention also includes a pharmaceutical composition which comprises an antibacterially effective amount of a compound of formula I and the pharmaceutically acceptable salts thereof in combination with a pharmaceutically acceptable carrier.

The invention further includes a method for treating bacterial infections in a mammal which comprises administering an antibacterially effective amount of a pharmaceutical composition as defined above to a mammal in need thereof.

The invention also includes novel processes for preparing compounds of formula I as illustrated and described hereinafter.

The invention further includes novel compounds which are intermediates in the above mentioned process having the names:

4-(4-bromo-2,5-difluorophenyl)-1-methyl-4-piperidinol;
4-(4-bromo-2,5-difluorophenyl)-1,2,3,6-tetrahydro-1 methylpyridine;
2,5-difluoro-4-(1,2,3,6-tetrahydro-1-methyl-4-pyridinyl)benzonitrile;
2,5-difluoro-4-(1-methyl-4-hydroxy-4-piperidinyl)benzoic acid;
2,5-difluoro-4-(1,2,3,6-tetrahydro-1-methyl-4-pyridinyl)benzoic acid;
2,5-difluoro-4-(1-methyl-4-piperidinyl)benzoic acid;
2,5-difluoro-4-(1-methyl-4-piperidinyl)benzoyl chloride, monohydrochloride;
ethyl 2,5-difluoro-4-(1-methyl-4-piperidinyl)-$\beta$-oxobenzenepropanoate;

ethyl α-(ethoxymethylene)-2,5-difluoro-4-(1-methyl-4-piperidinyl)-β-oxobenzenepropanoate;

ethyl α-[(cyclopropylamino)methylene]-2,5-difluoro-4-(1-methyl-4-piperidinyl)-β-oxobenzenepropanoate;

1-benzyl-3-(4-bromo-2,5-difluorophenyl)-3-pyrrolidinol;

4-(4-bromo-2,5-difluorophenyl)-2,3-dihydro-1-benzyl-1H-pyrrole;

4-[4,5-dihydro-1-benzyl-1H-pyrrol-3-yl]-2,5-difluorobenzonitrile;

2,5-difluoro-4-(1-benzyl-3-hydroxy-3-pyrrolidinyl)benzoic acid;

2,5-difluoro-4-(1-benzyl-3-pyrrolidinyl)benzonitrile;

2,5-difluoro-4-(1-benzyl-3-pyrrolidinyl)benzoic acid;

2,5-difluoro-4-(1-benzyl-3-pyrrolidinyl)benzoyl chloride, monohydrochloride;

ethyl 2,5-difluoro-4-(1-benzyl-3-pyrrolidinyl)-β-oxobenzenepropanoate;

ethyl α-(ethoxymethylene)-2,5-difluoro-4-(1-benzyl-3-pyrrolidinyl)-β-oxobenzenepropanoate; and ethyl α-[(cyclopropylamino)methylene]-2,5-difluoro-4-(1-benzyl-3-pyrrolidinyl)-β-oxobenzenepropanoate.

DETAILED DESCRIPTION

The alkyl groups contemplated by the invention such as alkyl per se, alkylthio, arylalkyl, or alkylaryl, are both straight and branched carbon chains of from one to about six carbon atoms unless otherwise stated. Representative of such groups are methyl, ethyl, propyl, n-propyl, 2-butyl, isobutyl, n-hexyl, and the like. The alkyl groups may be substituted or unsubstituted by halogen, hydroxy, carboxyl, amino, carboxamido, or the like or as specified.

The cycloalkyl groups contemplated by the invention are those having from three to about six carbon atoms unless otherwise stated. Representative of such groups are cyclopropyl, cyclobutyl, cyclopentyl, cyclohexyl, and the like. The cycloalkyl groups may be unsubstituted or substituted by hydroxy, alkyl, aryl, aryl substituted by alkyl, alkoxy, or halogen, or as specified.

The alkoxy groups contemplated by the invention comprise both straight and branched carbon chains of from one to about six carbon atoms unless otherwise specified. Representative of such groups are methoxy, propoxy, i-propoxy, t-butoxy, hexoxy, and the like. The alkoxy groups may be unsubstituted or substituted by carboxy, amino, or hydroxy, or as specified.

The term halogen is intended to include fluorine, chlorine, bromine, and iodine.

The term aryl is intended to include substituted or unsubstituted phenyl, naphthyl, biphenyl, indanyl, indolyl, quinolyl, or isoquinolyl. The substituents include one or more substituents such as halogen, nitro, alkyl, alkoxy, alkylthio, hydroxy, or others as specified.

The term heteroaryl per se, or as in arylalkyl or alkylaryl, is as described above for the term aryl but now includes a heteroatom such as nitrogen, sulphur, or oxygen in the ring. Representative of such groups are pyridine, imidazole, thiophene, furan, or as otherwise specified.

The term alkenyl as contemplated by the invention includes carbon groups of from two to about six carbon atoms containing a double bond. Representative of such groups are vinyl, allyl, methallyl and the like.

The term alkanoyl as contemplated by the invention includes carbon chains of from one to three carbon atoms except as otherwise specified. Examples are formyl, acetyl, propionyl, and the like.

Peptides contemplated by the instant invention comprise the naturally occurring α-amino acids: glycine, alanine, valine, leucine, isoleucine, phenylalanine, aspargine, glutamine, tryptophan, proline, hydroxyproline, serine, threonine, tyrosine, cysteine, cystine, methionine, aspartic acid, glutamic acid, lysine, arginine, histidine, and their D-conformers and additional analogs as defined

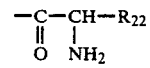

where $R_{22}$ is also defined as trimethylene or hydroxy substituted trimethylene when taken together with the nitrogen atom of the amine group one terminal methylene is bonded to the α-amino group to form acyl groups derived from proline or hydroxyproline, except as where stated to be otherwise.

The amidines contemplated by the invention are of the formula (alkyl-), (aryl-), (alkylaryl-) or

and include formamidine, acetamidine, alkylamidines, arylamidines, alkylarylamidines, and the like except as where otherwise specified.

The compounds of formula I are prepared according to a process which comprises:

(a) lithiating a compound of the formula

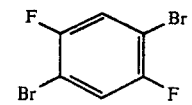

with an alkyl lithiating agent to give an organo lithium reagent compound of the formula

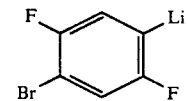

(b) reacting the above compound with a carbocyclic ketone or heterocyclic ketone of the formula

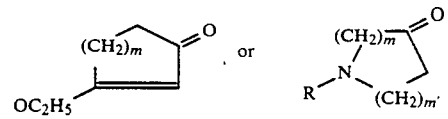

wherein m and m' are each independently 1 or 2 and R is lower alkyl or benzyl to give a compound

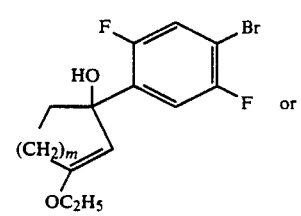

-continued

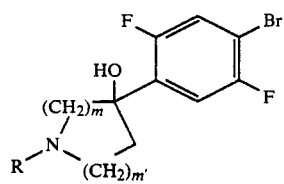

(c) dehydrating a compound of step (b) above to give an olefin derivative

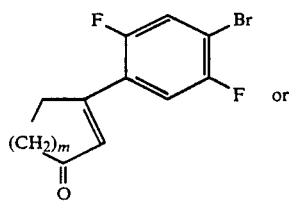 or

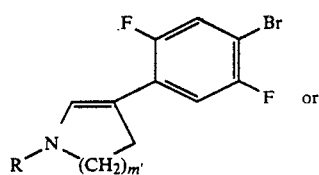 or

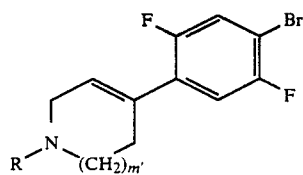

(d) reducing a compound of step (c) to give a saturated compound of formula

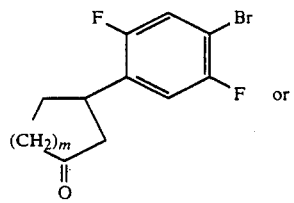 d or

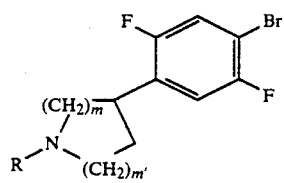 d¹

(e) converting a compound of formula (d) above into a corresponding ketal and carboxylating the product to produce a compound of formula

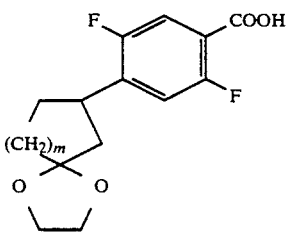

(f) carboxylating a compound of formula d¹ in step (d) above to give a compound of the formula

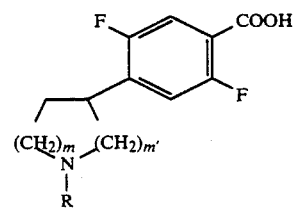

(g) reacting a carboxylated compound of step (e) or (f) above with carbonyldiimidazole to produce a compound of formula

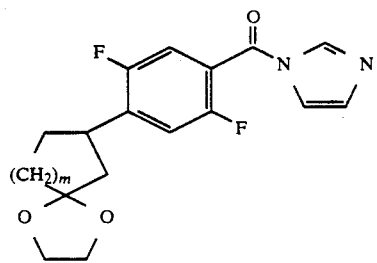

or

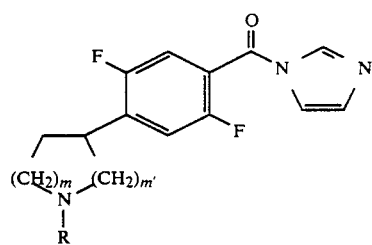

(h) reacting an imidazolide from step (g) with a dianion of monoethyl malonate to give a keto ester of formula

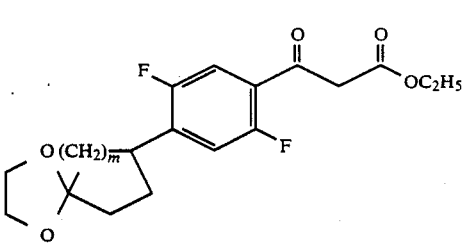

or

-continued

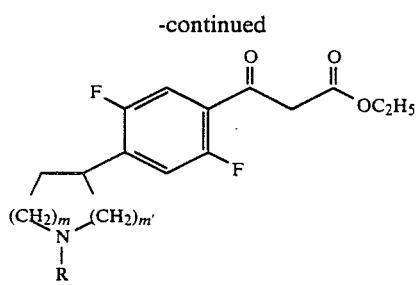

(i) reacting a keto ester from step (h) above with triethyl orthoformate in acetic anhydride to give an adduct of the formula

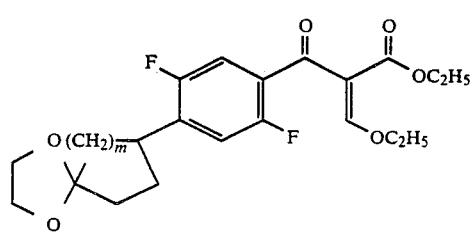

or

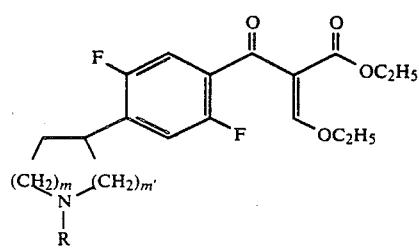

(j) reacting an adduct from step (i) with a primary amine in a polar solvent to produce an amine containing compound of formula

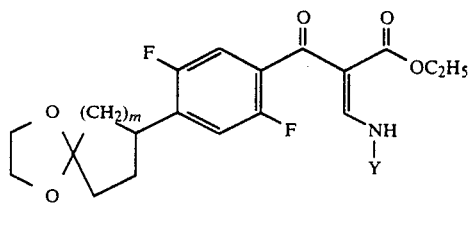

or

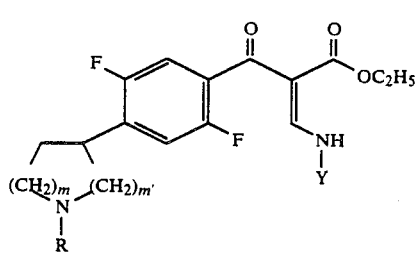

wherein Y is alkyl such as ethyl and the like, cycloalkyl such as cyclopropyl and the like, aryl such as p-fluorophenyl, 2,4-difluorophenyl, and the like, and heteroaryl such as 2-aminopyridyl, 3-aminopyridyl, 4-aminopyridyl, and the like;

(k) closing the ring in an amine-containing compound from step (j) by adding a strong, hindered base to give a compound of the formula

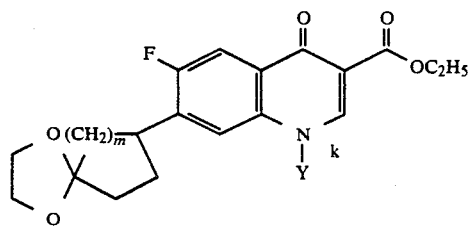

or

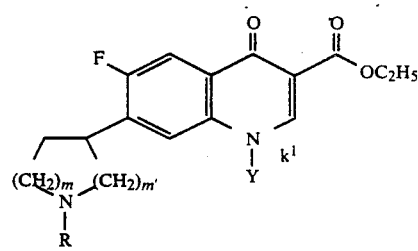

and deprotecting compound $K^1$ when R is benzyl to give a desired compound of formula I and converting, if desired, to a pharmaceutically acceptable acid addition salt or the free acid, (l) hydrolyzing the ketal and ester functionalities of a compound k in step (k) above to give a keto acid of the formula

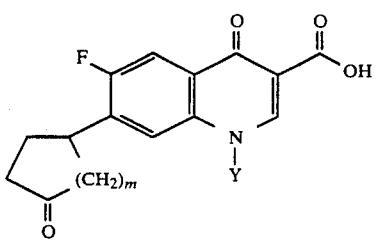

(m) converting the keto acid of above step (l) to the corresponding oxime and then reducing the oxime to give the desired amino acid of formula I and converting, if desired, to a pharmaceutically acceptable acid addition salt thereof.

Compounds of formula II can be prepared in analogous manner with the exception of the reduction step (d).

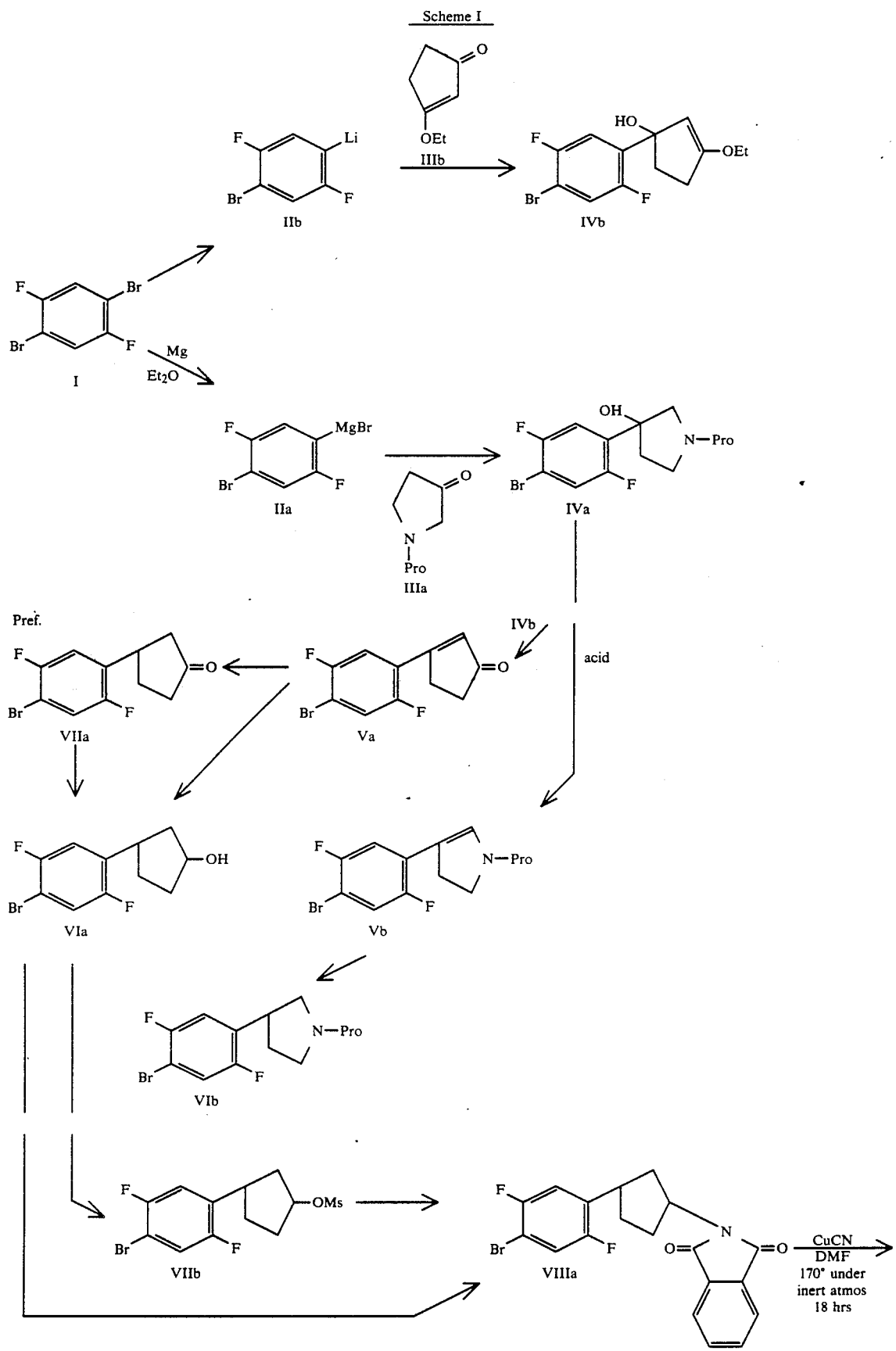

-continued
Scheme I
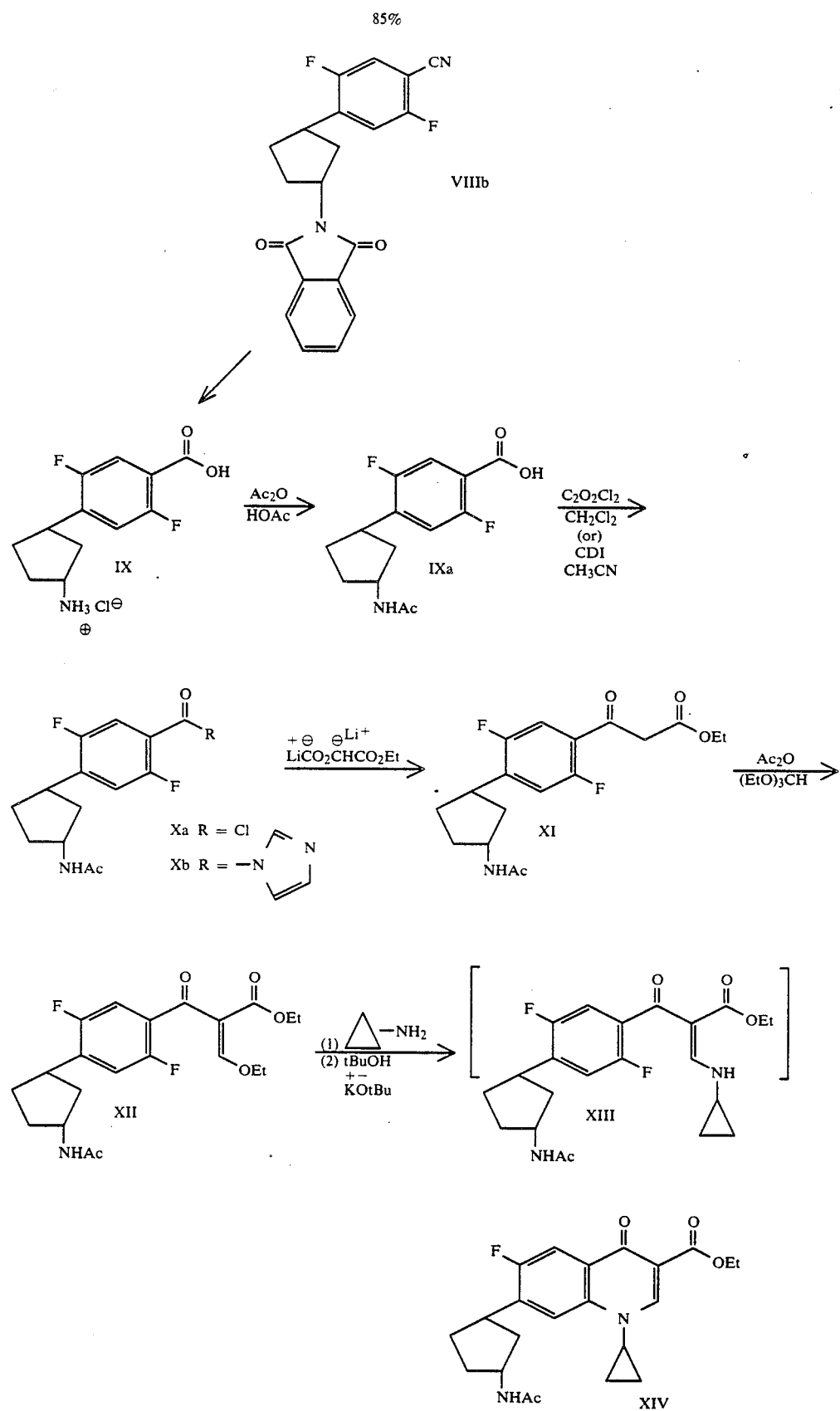

-continued
Scheme I

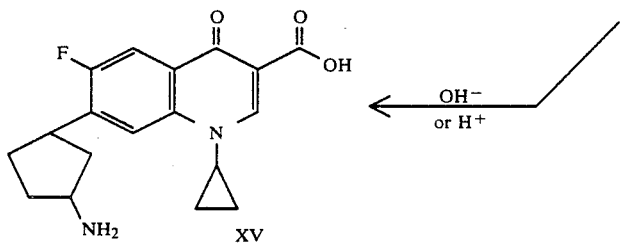

The compound (I), of the above Scheme I 1,4-dibromo-2,5-difluorobenzene, is converted to the Grignard (IIa) by reaction with magnesium in an organic solvent such as ether or tetrahydrofuran. The Grignard is reacted with a cyclic ketone (IIIa) to form the corresponding alcohol (IVa). Alternatively compound (I) may be reacted with n-butyl lithium in tetrahydrofuran to form the organo lithium reagent (IIb). This reagent can be reacted with a cyclic ketone to form the corresponding alcohol of the type (IVb). The alcohols produced (for example, IVa and IVb) can be dehydrated under acid catalyzed conditions such as aqueous acid or an organic acid in a solvent such as toluene using a Dean-Stark trap to form the corresponding alkenes (Va) and (Vb). The alkene is reduced to the corresponding saturated compounds (VIb) and (VIIa) using hydrogen and a metal catalyst in an organic solvent, for example, Wilkinson's in tetrahydrofuran (THF). If desired, the alkene (Va) can be reduced to the saturated alcohol (VIa) using a metal hydride in an organic solvent, for example, sodium borohydride in pyridine. Alternatively the ketone (VIIa) can be converted to the alcohol (VIa) using a metal hydride in a solvent, for example, sodium borohydride in methanol. The alcohol (VIa) can be converted to a protected amino group (VIIIa) directly using the known Mitsunobo reaction (*Synthesis*, 1981, 1). Alternatively the alcohol compound VIa can be converted to the tosylate or mesylate derivative (VIIb). A displacement reaction with potassium phthalimide in a polar solvent such as dimethylsulfoxide or N,N-dimethylformamide converts these derivatives to the protected amino compound (VIIIa).

This derivative is then reacted with copper (I) cyanide in dimethylformamide (DMF) to form the nitrile (VIIIb) which is subsequently completely hydrolyzed to the amino acid compound (IX). This compound (IX), after acetylation to reprotect the amine function, gives (IXa), which is converted to the acid chloride (Xa) or the imidazolide (Xb). Either derivative (Xa or Xb) can then be reacted with the preformed dianion of monoethyl malonate, prepared from monoethyl malonic acid and n-butyl lithium in THF, to produce the keto ester (XI). This is reacted with triethyl orthoformate in acetic anhydride to form the diethylethoxymethylenemalonate (EMME) adduct XII. This adduct is then reacted with a primary amine in a solvent such as t-butanol to produce the enamine (XIII). Primary amines can be aliphatic amines (such as cyclopropylamine, ethylamine, etc.), aromatic amines (such as p-fluoroaniline, 2,4-difluoroaniline, etc.) or heteroaromatic amines (such as 2-aminopyridine, 3-aminopyridine, 4-aminopyridine, etc.). These compounds are reacted with potassium t-butoxide in a solvent such as t-butanol forming the desired cyclized nitrogen containing compound XIV. The amine protecting group and the ester can be removed by either acid or base hydrolysis to give the final product (XV).

Scheme II

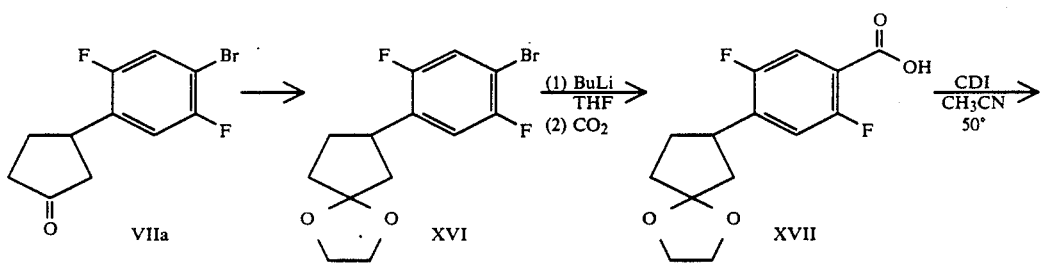

-continued
Scheme II

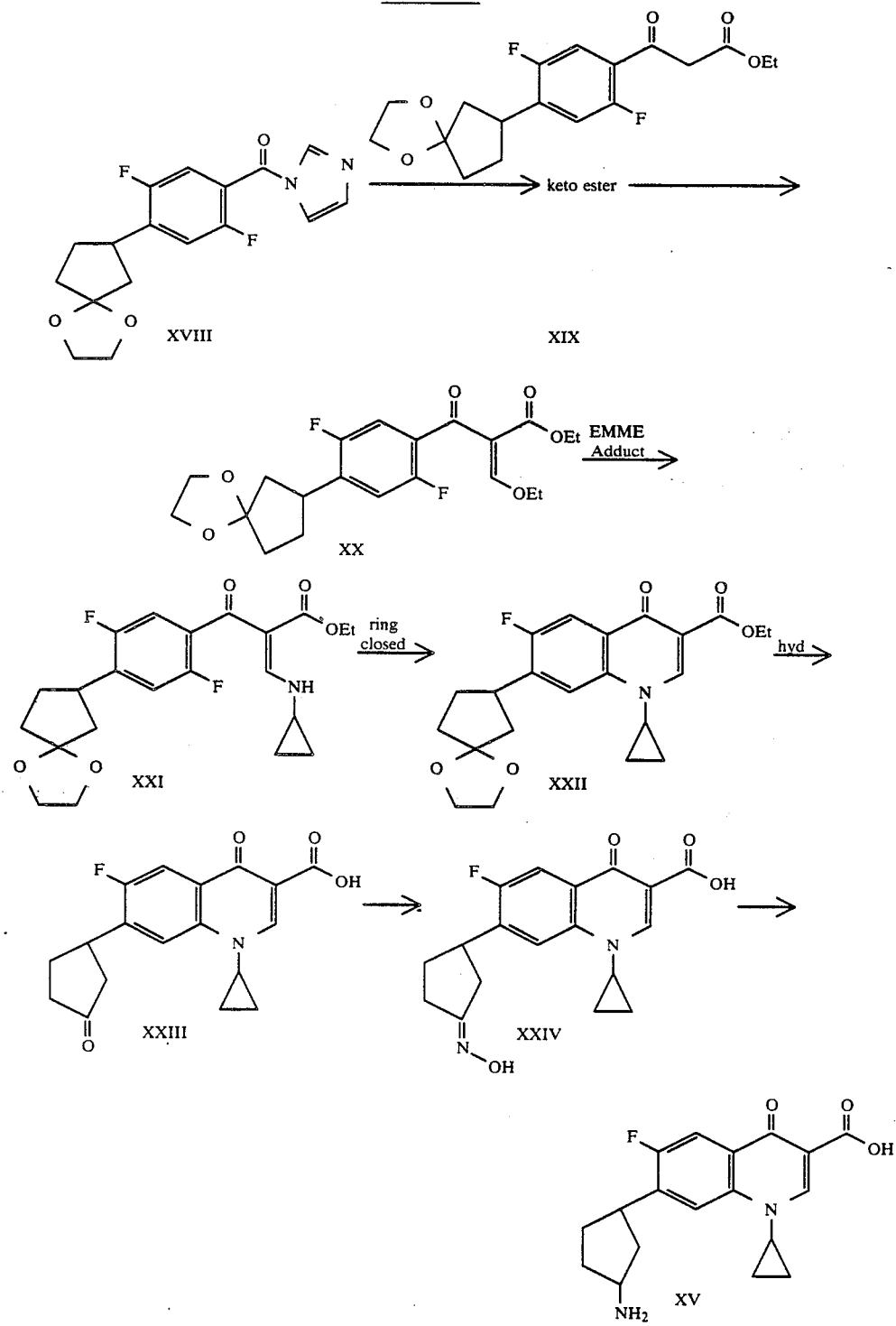

Alternately (Scheme II) as shown above, the saturated ketone (VIIa) (Scheme I) can be protected as the ketal (XVI) using ethylene glycol in a high boiling aromatic hydrocarbon solvent such as toluene and an acid catalyst such as p-toluene sulfonic acid, removing the water using a Dean-Stark trap. The ketal (XVI) can be lithiated at low temperature (−78° C.) using n-butyl lithium in an anhydrous solvent such as THF and carbonating the organo lithium reagent using a form of carbon dioxide (either gaseous or dry ice) to give the acid, (XVII). The acid (XVII) can be converted to the imidazolide (XVIII) by reaction with 1,1′-carbonyl-diimidazole in a solvent such as acetonitrile at ambient temperatures (50° C.). The imidazolide can be reacted with the preformed dianion of monoethyl malonate prepared as in Scheme I to give the keto ester, (XIX). The keto ester (XIX) can be reacted with triethyl orthoformate in acetic anhydride at reflux to give the EMME adduct, (XX). The EMME adduct (XX) can be reacted with a primary amine such as those described in Scheme I, in a polar solvent such as t-butanol to produce the enamine, (XXI). Ring closure to (XXII) can then be effected by the addition of a strong, hindered base such as potassium t-butoxide to the enamine in t-butanol. Hydrolysis of the ketal and ester functionalities using acid catalysis gives the keto acid (XXIII). The ketone can be converted to the oxime (XXIV) using hydroxylamine hydrochloride, a base such as potassium carbonate and a polar solvent such as aqueous ethanol. The oxime can then be reduced using hydrogen on a catalyst such as Raney-nickel in a polar solvent such as DMF to give the desired amino acid (XV).

Scheme III

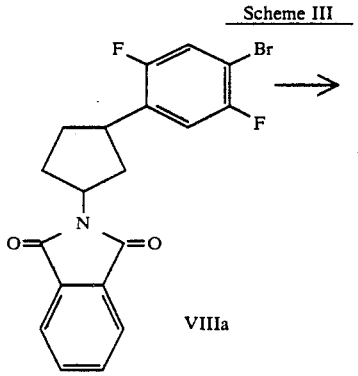

VIIIa

From displacement of mesylate or Mitsunobo

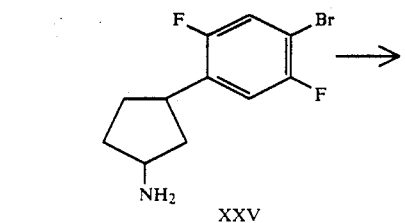

XXV

-continued
Scheme III

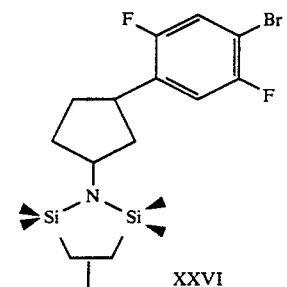

XXVI (1) BuLi
(2) CO₂
(3) Deprotect with 1.0 M HCl

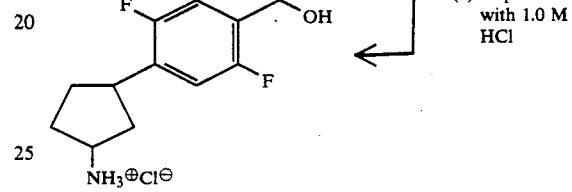

IX

See Scheme I

In an alternate sequence of reactions (Scheme III) above the desired intermediate amino acid (IX) can be prepared from (VIIIa) by removing the amine protecting group using hydrazine in a polar solvent such as methanol to give the free amino compound (XXV). This compound can be reprotected as the silyl derivative (XXVI) which is impervious to n-butyl lithium. This permits (XXVI) to be lithiated using n-butyl lithium in a solvent such as THF with subsequent carbonation using carbon dioxide in either gaseous or solid form (dry ice) to give the desired amino acid (IX) which can be converted to the desired final product (XV) by the sequence of reactions outlined in Scheme I.

Scheme IV

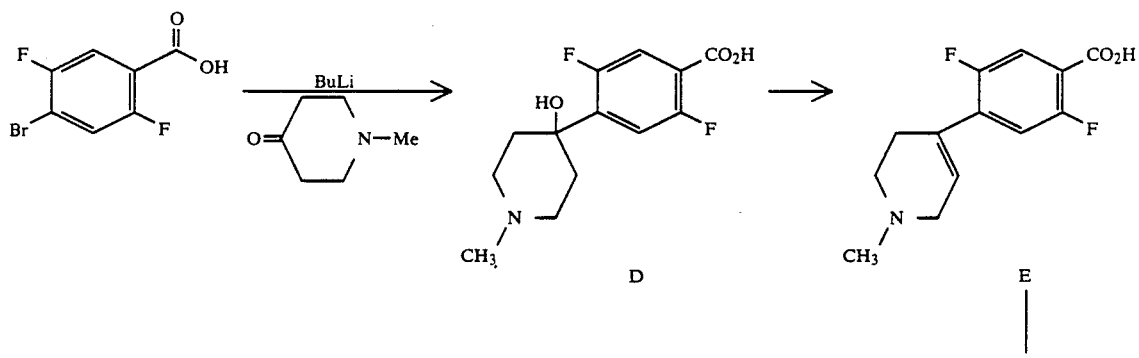

-continued
Scheme IV
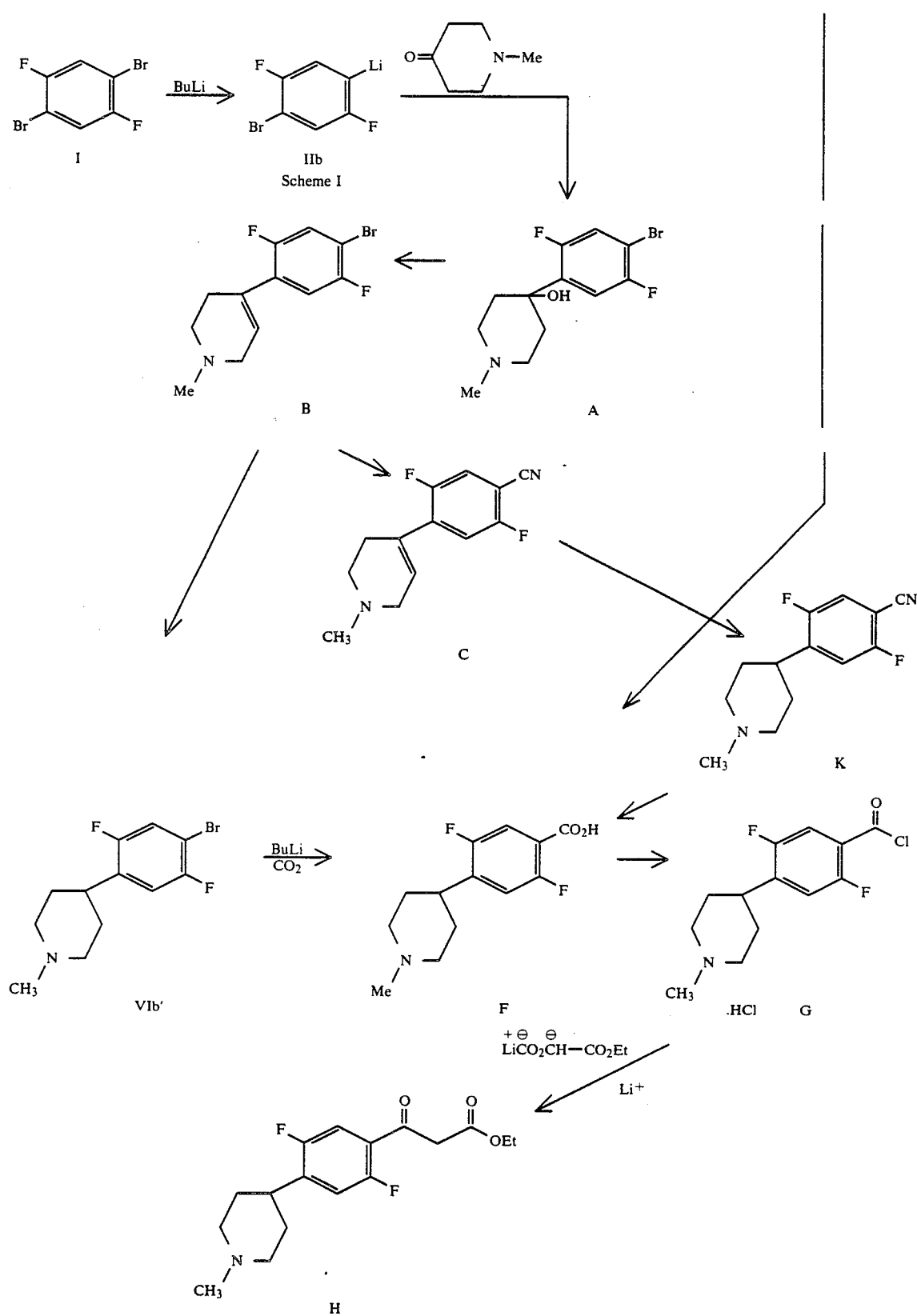

-continued
Scheme IV

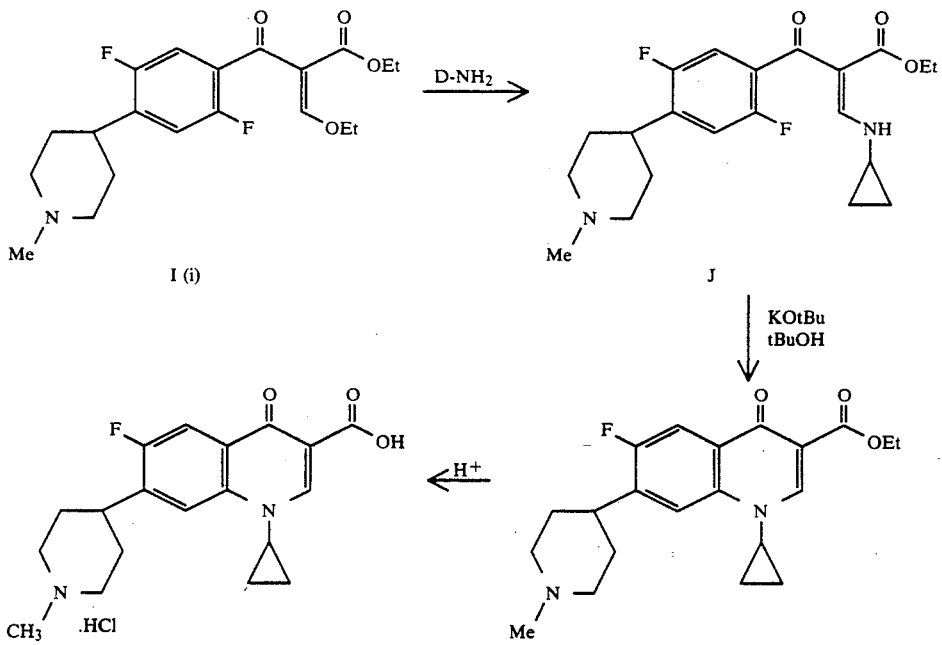

The compound (D) of Scheme IV above, 2,5-difluoro-4-(1-methyl-4-hydroxy-4-piperidinyl)benzoic acid, is prepared by reacting 1-methyl-4-piperidone with the dianion of 4-bromo-2,5-difluorobenzoic acid [Kogyo Kagaku Zasshi, 73, 972 (1970)] which is in turn prepared by the action of n-butyl lithium in tetrahydrofuran. The alcohol can then be dehydrated to the alkene (E) by refluxing in 6.0 M hydrochloric acid. Hydrogenation of the alkene using 10% palladium on carbon in water gives the saturated compound F.

Alternatively F can be prepared starting with 1,4-dibromo-2,5-difluorobenzene (Compound I, Scheme I). The anion (IIb - Scheme I) is prepared by reaction with butyl lithium in tetrahydrofuran and then addition of 1-methyl-4-piperidone to give the alcohol A. Dehydration in refluxing 6.0 M hydrochloric acid gives the alkene B. Displacement of the second bromine using copper (I) cyanide in refluxing N,N-dimethylformamide gives the nitrile C. The alkene can be reduced to the saturated compound K using Wilkinson's catalyst in tetrahydrofuran. Hydrolysis of the nitrile in refluxing 6.0 M hydrochloric acid gives the acid F.

Compound F can also be prepared from the bromoalkene B by first reducing to the saturated bromo compound VIb[1] (which is the six membered analog of VIb - (Scheme I) using Wilkinson's catalyst in tetrahydrofuran. Preparation of the anion using butyl lithium in tetrahydrofuran followed by carbonation using gaseous carbon dioxide or dry ice gives the acid F.

The amino acid (F) is converted to the acid chloride hydrochloride (G) by refluxing in thionyl chloride. The keto ester (H) can then be prepared by reacting the neutralized amino acid chloride with the preformed dianion of monoethyl malonic acid (prepared from mono ethyl malonic acid and n-butyl lithium in tetrahydrofuran). This is reacted with triethyl orthoformate in acetic anhydride to give the EMME adduct I. This adduct is then reacted with a primary amine in a solvent such as t-butanol to produce the enamine J. Primary amines can be amines such as those described for the enamine XIII (scheme II). Reaction with a base such as potassium t-butoxide in a solvent such as t-butanol form the desired, cyclized nitrogen containing compound (Ex. 1). The ester is hydrolyzed and the amine is converted to the hydrochloride salt by refluxing in 6.0 M hydrochloric acid and evaporating the resulting solution to dryness to give the desired final product.

It has been found that certain compounds of the present invention can best be made by the process of U.S. application Ser. No. 275,149, filed Nov. 22, 1988, now allowed, and its divisional, 502,004, filed Mar. 29, 1990. These applications are hereby incorporated by reference. The compounds made by the process are compounds of formula I named:

1-cyclopropyl-6-fluoro-1,4-dihydro-4-oxo-7-(1,2,3,6-tetrahydro-4-pyridinyl)-1,8-naphthyridine-3-carboxylic acid, 1-cyclopropyl-6-fluoro-1,4-dihydro-4-oxo-7-(3-aminocyclopent-1-enyl)-1,8-naphthyridine-3-carboxylic acid, 1-cyclopropyl-6-fluoro-1,4-dihydro-4-oxo-7-[1-methyl-3-pyrrolidinyl]-1,8-naphthyridine-3-carboxylic acid, 1-(2,4-difluorophenyl)-6-fluoro-1,4-dihydro-4-oxo-7-(3-amino-1-cyclopentenyl)-1,8-naphthyridine-3-carboxylic acid, 1-cyclopropyl-6-fluoro-1,4-dihydro-4-oxo-7-(3-amino-1-cyclohexenyl)-1,8-naphthyridine-3-carboxylic acid, and 1-(2,4-difluorophenyl)-6-fluoro-1,4-dihydro-4-oxo-7(1,2,3,6-tetrahydro-4-pyridinyl)-1,8-naphthyridine-3-carboxylic acid.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, lactic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

Certain compounds of the invention may exist in optically active forms. The pure R isomer, pure S isomer as well as mixtures thereof, including the racemic mixtures, are contemplated by the invention. Additional asymmetric carbon atoms may be present in a substituent such as alkyl group. The presence of an α-amino acid group on the compounds of the present invention means they all exist in optically active forms. The pure D isomer, pure L isomer as well as mixtures thereof, including the racemic mixtures, are contemplated by the invention. The individual D and L isomers are preferably prepared by using the naturally occurring L-α-amino acids or their D-conformers and, in the case of other α-amino acids, resolving such acids by known means, then reacting them by methods of standard peptide chemistry.

An additional asymmetric carbon atom may be present in the Z portion of the compounds of formula I. Thus the compounds of formula I may have two asymmetric carbon atoms and four optical isomers where both asymmetric carbon atoms reside in the Z group. All such isomers, diastereomers, enantiomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I or Ia or a corresponding pharmaceutically acceptable salt of a compound of formula I or Ia.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compounds of the invention display antibacterial activity when tested by the microtitration dilution method as described by Heifetz et al, Antimicr. Agents & Chemoth., 6, 124 (1974), which is incorporated herein by reference.

The following nonlimiting examples illustrate the invention.

PREPARATION OF STARTING MATERIALS

Example A 4-(4-Bromo-2,5-difluorophenyl)-1-methyl-4-piperidinol

A solution of 2.72 g (10 mmoles) of 1,4-dibromo-2,5-difluorobenzene in 50 ml of ethyl ether, under an argon atmosphere stirred at −75° C., was treated dropwise with 4.2 ml of 2.5 M n-butyl lithium (hexane solution). The mixture was treated dropwise with a solution of 1.20 g (10.6 mmoles) of N-methyl-4-piperidone in 10 ml of ethyl ether, stirred a further 0.75 hours at −75° C., let warm to −30° C., and poured into a solution of 0.56 g (10.5 mmoles) ammonium chloride in 15 ml of water. The ether layer was washed with two 10 ml portions of water, dried (MgSO$_4$), and evaporated to give 2.85 g of crude product which was purified by chromatography on a column of silica gel and crystallized to give 1.30 g of the title compound; mp 133°–135° C.

Example B 4-(4-Bromo-2,5-difluorophenyl)-1,2,3,6-tetrahydro-1-methylpyridine A solution of 0.92 g (3 mmoles) of 4-(4-bromo-2,5-difluorophenyl)-1-methyl-4-piperidinol in 20 ml of 6 N hydrochloric acid was refluxed 4 hours, and evaporated to dryness under vacuum. The residue was stirred with ethyl ether and filtered to afford 0.97 g of the title compound; mp 223°–233° C. with decomposition.

Example C 2,5-Difluoro-4-(1,2,3,6-tetrahydro-1-methyl-4-pyridinyl) benzonitrile A mixture of 2.88 g (10 mmoles) of 4-(4-bromo-2,5-difluorophenyl)-1,2,3,6-tetrahydro-1-methylpyridine and 0.90 g (10 mmoles) of cuprous cyanide in 30 ml of dimethylformamide was refluxed overnight. The solvent was evaporated, the residue treated with ammonium hydroxide, and the solution extracted with dichloromethane. Evaporation of the organic phase afforded the title compound.

Example D 2,5-Difluoro-4-(1-methyl-4-hydroxy-4-piperidinyl)benzoic acid

A solution of 1.19 g (5 mmoles) of 4-bromo-2,5-difluorobenzoic acid in 20 ml of tetrahydrofuran at −75° C. was treated with 4.2 ml of 2.4 M n-butyl lithium in hexane. The mixture was stirred 20 minutes, treated with a solution of 0.58 g (5.1 mmoles) of 1-methyl-4-piperidone in 5 ml tetrahydrofuran, stirred a further 1.5 hours, let warm to −30° C., and treated with a solution of 0.55 g (10.3 mmoles) ammonium chloride in 20 ml water. The product, the title compound, crystallized on standing.

Example E 2,5-Difluoro-4-(1,2,3,6-tetrahydro-1-methyl-4-pyridinyl)benzoic acid hydrochloride 2.34 g (10 mmoles) of 2,5-difluoro-4-(1,2,3,6-tetrahydro-1-methyl-4-pyridinyl)benzonitrile in 100 ml of 6 N hydrochloric acid was refluxed overnight, and the mixture was concentrated to afford the title compound.

Example F 2,5-Difluoro-4-(1-methyl-4-piperidinyl)benzoic acid 2.53 g (10 mmoles) of 2,5-difluoro-4-(1,2,3,6-tetrahydro-1-methyl-4-pyridinyl)benzoic acid hydrochloride in 100 ml water with 10% Pd/C catalyst was hydrogenated under pressure. Filtration and evaporation afforded the title compound.

Example G 2,5-Difluoro-4-(1-methyl-4-piperidinyl)benzoyl chloride hydrochloride 2.91 g (10 mmoles) of 2,5-difluoro-4-(1-methyl-4-piperidinyl)benzoic acid hydrochloride was refluxed with thionyl chloride and evaporated to afford the title compound.

Example H

Ethyl 2,5-difluoro-4-(1-methyl-4-piperidinyl-β-oxobenzenepropanoate

A solution of 3.90 g (30 mmoles) of malonic acid monoethyl ester in 50 ml of tetrahydrofuran at −30° C. was treated with 18.8 ml of 1.6 M n-butyl lithium in hexanes. The temperature was raised to −10° C. and again treated with 18.8 ml of 1.6 M n-butyl lithium solution. The mixture was recooled to −78° C. and treated with 3.10 g (10 mmoles) of 2,5-difluoro-4-(1-methyl-4-piperidinyl)benzoyl chloride hydrochloride. After stirring 1 hour and then warming to −30° C., the mixture was poured into water and concentrated hydrochloric acid. The organic phase was separated and washed with water, 5% sodium bicarbonate, dilute hydrochloric acid, and water. After drying, the solvent was removed in vacuo to give the title compound.

Example I

Ethyl α-(ethoxymethylene)-2,5-difluoro-4-(1-methyl-4-piperidinyl)-β-oxobenzenepropanoate A solution of 3 25 g (10 mmoles) of ethyl 2,5-difluoro-4-(1-methyl-4-piperidinyl)-β-oxobenzenepropionate in 20 ml of acetic anhydride and 2.5 ml of triethyl orthoformate was refluxed 1¼ hours and evaporated under vacuum to give the title compound.

Example J

Ethyl α-[(cyclopropylamino)methylene]-2,5-difluoro-4-(1-methyl-4-piperidinyl)-β-oxobenzenepropanoate A solution of 3.81 g (10 mmoles) of ethyl α-(ethoxymethylene)-2,5-difluoro-4-(1-methyl-4-piperidinyl)-β-oxobenzenepropanoate in 50 ml of ether was treated with 0.60 g (10 mmoles) of cyclopropylamine. After standing overnight the mixture was evaporated to dryness to afford the title compound.

Example K

1-Bromo-4 TM (3-chlorocyclopentyl)-2,5-difluorobenzene

A solution of 27.7 g (0.1 mol) of 3-(4-bromo-2,5-difluorophenyl)cyclopentanol in 150 ml of thionyl chloride was heated at reflux until gas evolution ceased (4 hours). The solvent was removed in vacuo and the residue was triturated with toluene (2×200 ml) which was also removed in vacuo. The residue was dissolved in ether, washed with water (3×100 ml), dried (MgSO$_4$), filtered, and evaporated in vacuo to give 26.2 g of the title compound which was used without further purification.

Example L 3-(4'-Bromo-2',5'-difluorophenyl)-2-cyclopentenone

A solution of 27.2 g (0.1 mole) of 1,4-dibromo-2,5-difluorobenzene in 200 ml of ether was blanketed with argon and cooled to −78° C. To this mixture was added 42 ml of n-butyl lithium (2.4 M; 0.10 mole) dropwise via an addition funnel. The solution was stirred at −78° C. for 15 minutes, then allowed to warm to −45° C. To the anion was added 13 ml of 3-ethoxy-2-cyclopentenone (0.10 mole); the solution was kept at −45° for 30 minutes and was then warmed slowly to room temperature. The mixture was poured into 250 ml of 1 N hydrochloric acid, stirred for 30 minutes, and extracted with ethyl acetate; the organic phases were combined, washed with water, dried over magnesium sulfate, and concentrated. The crude product was purified via silica gel chromatography using an 80:20 chloroform ethyl acetate mixture to give 14.2 g of the desired product; mp 129°–131° C.

Example M 3-(4-Bromo-2,5-difluorophenyl)cyclopentanone

A solution of 16.4 g (60.2 mmol) of 3-(4-bromo-2,5-difluorophenyl)-2-cyclopentenone in 400 ml of THF was hydrogenated over 2.0 g of Wilkinson's catalyst at 25° C. for 18 hours. The solution was concentrated to a brown oil which was chromatographed on silica gel (E. Merck-230–400 Mesh) to remove the catalyst. The residue obtained was triturated with hexane, and the solids were filtered, washed with hexane, and dried to give 15.2 g (93%) of the title compound; mp 63°–65° C.

Example N 3-(4-Bromo-2,5-difluorophenyl)cyclopentanol

To 15.0 g (54.5 mmol) of 3-(4-bromo-2,5-difluorophenyl) cyclopentanone in 150 ml of absolute ethanol and 10 ml of THF was added 2.5 g (65.4 mmol) of sodium borohydride portionwise. The reaction mixture was stirred for 2½ hours at room temperature, then poured into a mixture of 250 ml of 1.0 N NaOH and 250 ml of ethyl acetate. The organic phase was washed with water, dried (MgSO$_4$), and concentrated. The crude product was chromatographed over silica gel, eluting with 80:20 CHCl$_3$:EtOAc, to give 10.8 g (72%) of the desired product as a yellow oil.

Example O

2-[3-(4-Bromo-2,5-difluorophenyl)cyclopentyl]-1H-isoindole-1,3(2H)-dione

A solution of 29.6 g (0.1 mol) of 1-bromo-4-(3-chlorocyclopentyl)-2,5-difluorobenzene in 150 ml of dry dimethylformamide was treated with 19.4 g (0.105 mol) of potassium phthalimide and the resulting suspension stirred at 100° for 8 hours and room temperature overnight. The solvent was removed in vacuo, and the residue was partitioned between methylene chloride and water. The aqueous layer was reextracted with methylene chloride and the combined organic layers were washed with water, dried (MgSO$_4$), filtered, and evaporated in vacuo to give 36.8 g of the title compound as a viscous oil which crystallized on standing and had mp 44°–47°.

Example P

2-[3-(4-Bromo-2,5-difluorophenyl)cyclopentyl]-1H-isoindole-1,3(2H)-dione

To a solution of 13.9 g (50 mmol) of 3-(4-bromo-2,5-difluorophenyl)cyclopentanol, 7.4 g (50 mmol) of phthalimide and 13.1 g (50 mmol) of triphenylphosphine in 50 ml of dry tetrahydrofuran was added dropwise at room temperature a solution of 8.7 g (50 mmol) of diethyl azodicarboxylate in 20 ml of dry tetrahydrofuran. The reaction was stirred at room temperature for 18 hours and the solvent was removed in vacuo. The residue was triturated with ether and the solid removed by filtration. The filtrate was evaporated in vacuo and the residue was chromatographed on silica gel (E. Merck - 230–400 Mesh) eluting with chloroform-ethyl acetate (4:1) to give 15.6 g of the title compound; mp 47°–48°.

Example Q

4-[3-(1,3-Dihydro-1,3-dioxo-2H-isoindol-2-Yl)cyclopentyl]-2,5-difluorobenzonitrile A suspension of 91.35 g (0.225 mol) of 2-[3-(4-bromo-2,5-difluorophenyl)cyclopentyl-1H-isoindole-1,3-(2H)-dione, 22.4 g (0.25 mol) of copper (I) cyanide and 250 ml of N,N-dimethylformamide was stirred and heated in a nitrogen atmosphere at 170° for 18 hours. The cooled mixture was poured into a solution of 100 ml of concentrated ammonium hydroxide in 1 L of water. The aqueous mixture was extracted with ether (4×350 ml) and the combined ether layers were washed with water (3×300 ml), dried (MgSO$_4$), and evaporated in vacuo to give 71.2 g of the title compound which was used as is for the next step.

Example R

4-[3-(Amino)cyclopentyl]-2,5-difluorobenzoic acid

A solution of 35.2 g (0.1 mol) of 4-[3-(1,3-dihydro-1,3-dioxo-2H-isoindol-2-yl)cyclopentyl]-2,5-difluorobenzonitrile in 150 ml of 98% sulfuric acid was heated at 100° for 6 hours. The reaction mixture was poured onto 1.2 L of ice and water and stirred for 2 hours until the granular precipitate dispersed. The solid was removed by filtration, washed with water and the wet filter cake suspended in 200 ml of concentrated hydrochloric acid. The suspension was heated at reflux for 8 hours and evaporated to dryness in vacuo. The residue was triturated with 250 ml of ethanol/ether (1:1); the solid was removed by filtration, washed with ethanol/ether (1:1), ether, and dried in vacuo to give 20.1 g of the title compound.

Example S

4-[3-(Acetylamino)cyclopentyl]-2,5-difluorobenzoic acid

A solution of 24.1 g (0.1 mol) of 4-[3(amino)cyclopentyl]-2,5-difluorobenzoic acid in a mixture of 50 ml of acetic anhydride and 100 ml of acetic acid was heated at reflux for 6 hours. The solvent was removed in vacuo and the residue triturated with water. The solid was removed by filtration, washed with water, and dried in vacuo to give 25.3 g of the title compound.

Example T

4-[3-(Acetylamino)cyclopentyl]-2,5-difluorobenzoyl chloride

A mixture of 14.2 g (50 mmole) of 4-[3-(amino)cyclopentyl]-2,5-difluorobenzoic acid in 200 ml of methylene chloride was treated with 6.4 g (50 mmol) of oxalyl chloride and 0.5 ml of dimethylformamide. The reaction mixture was stirred at room temperature for 18 hours and the solvent removed in vacuo. The residue was triturated with toluene which was also removed in vacuo. The residue was used without further purification.

Example U

4-[3-(Acetylamino)cyclopentyl]-2,5-difluoro-$\beta$-oxobenzenepropanoic acid, ethyl ester

A solution of 26.4 g (0.2 mol) of monoethyl malonate, 0.1 g of 2,2'-bipyridyl and 350 ml of dry tetrahydrofuran was cooled to $-35°$ under a nitrogen atmosphere and treated dropwise with 80 ml (0.2 mol) of a 2.5 M solution of n-butyl lithium in hexane. After the addition was complete, the reaction mixture was allowed to warm to $-5°$ where it was treated dropwise with 80 ml (0.2 mol) of 2.5 M n-butyl lithium in hexane, titrating the final addition to a pale pink color which persisted for 5 minutes. The mixture was cooled to $-78°$ and treated with a solution of 30.2 g (0.1 mol) of 4-[3-(acetylamino) cyclopentyl]-2,5 difluorobenzoyl chloride in 150 ml of dry tetrahydrofuran. The suspension was stirred at $-78°$ for 45 minutes, then allowed to warm to $-35°$ and poured into a mixture of ice, water, and concentrated hydrochloric acid (17 ml–0.20 mol). The organic phase was separated, washed with water, 5% sodium bicarbonate, dilute hydrochloric acid and water. After drying over magnesium sulfate, the solvent was removed in vacuo to give 31.8 g of the title compound.

Example V

4-3-(Acetylamino)cyclopentyl]-$\alpha$-(ethoxymethylene)-2,5-difluoro-$\beta$-oxobenzenepropanoic acid, ethyl ester

A solution of 17.7 g (50 mmol) of 4-[3-(acetylamino)-cyclopentyl-2,5-difluoro-$\beta$-oxobenzenepropanoic acid, ethyl ester, 11.1 g (75 mmol) triethyl orthoformate and 75 ml of acetic anhydride was refluxed for 3 hours. The solvent was removed in vacuo and the residue triturated with toluene which was also removed in vacuo, then in high vacuo at 50°. The residue, 20.1 g, was used without further purification.

Example W

4-[3-(Acetylamino)cyclopentyl]-$\alpha$-[(cyclopropylamino)methylene]-2,5-difluoro-$\beta$-oxobenzenepropanoic acid, ethyl ester

A solution of 20.5 g (50 mmol) of 4-[3-(acetylamino)-cyclopentyl]-$\alpha$-(ethoxymethylene)-2,5-difluoro-$\beta$-oxobenzenepropanoic acid, ethyl ester, in 100 ml of absolute ethanol was cooled to 10° and 3.4 g (60 mmole) of cyclopropylamine was added dropwise maintaining the temperature below 15° with an ice bath. After the addition was complete, the reaction was stirred at 5°–10° for 1.5 hours and then at room temperature for 1 hour. The resulting suspension was chilled to 5° and the solid removed by filtration and washed with ethanol and then hexane. The combined filtrate and washings were evaporated in vacuo and the residue was recrystallized from pentane to give 16.1 g of the title compound.

Example X

7-(4-Bromo-2,5-difluorophenyl)-1,4-dioxaspiro[4.4]nonane

A solution of 27.5 g (0.1 mol) of 3-(4-bromo-2,5-difluorophenyl)cyclopentanone, 18.6 g (0.3 mol) of ethylene glycol, 1 g of p-toluenesulfonic acid and 500 ml of toluene was heated at reflux with a Dean-Stark trap for 18 hours. The cooled solution was washed with 5% sodium bicarbonate solution ($2\times250$ ml), dried ($MgSO_4$), and evaporated in vacuo to give 28.2 g of the title compound which was used without further purification.

Example Y

2,5-Difluoro-4-(1,4-dioxaspiro[4.4]non-7-yl)benzoic acid

A solution of 31.9 g (0.1 mol) of 7-(4-bromo-2,5-difluorophenyl)-1,4-dioxaspiro[4.4]nonane in 300 ml of dry tetrahydrofuran, under an argon atmosphere at $-78°$ C., was treated with 40 ml (0.1 mol) of 2.5 M n-butyl lithium (hexane solution). The solution was warmed to $-40°$ and poured onto 500 g of finely crushed dry ice and the mixture allowed to stand until the dry ice evaporated (18 hours). The solvent was evaporated in vacuo and the residue partitioned between ethyl acetate/1.0 M hydrochloric acid (500 ml ea). The organic layer was washed with water, dried ($MgSO_4$), and evaporated in vacuo to give 18.9 g of the title compound.

Example Z

1-[4-(1,4-Dioxaspiro[4.4]non-7-yl)-2,5-difluorophenyl]-carbonyl]-1H-imidazole

A suspension of 28.4 g (0.1 mol) of 2,5-difluoro-4-(1,4-dioxaspiro[4.4]non-7-yl)benzoic acid in 250 ml of dry acetonitrile was treated with 16.2 g (0.1 mol) of 1,1' carbonyldiimidazole. After initial gas evolution ceased, the reaction mixture was heated at 60° C. for 2 hours and the solvent evaporated in vacuo to give 33.1 g of the title compound which was used without further purification.

Example AA

2,5-Difluoro-4-(1,4-dioxaspiro[4.4]non-7-yl)-$\beta$-oxobenzenepropanoic acid, ethyl ester

A solution of 16.4 g (0.2 mol) of monoethyl malonate, 0.1 g of 2,2'-bipyridyl and 175 ml of dry tetrahydrofuran was cooled to $-35°$ under a dry nitrogen atmosphere and treated dropwise with 80 ml (0.2 mol) of a 2.5 M solution of n-butyl lithium in hexane. After the addition was complete, the reaction mixture was allowed to warm to $-5°$ where it was treated dropwise with 80 ml (0.2 mol) of 2.5 M n-butyl lithium in hexane, titrating the final addition to a pale pink color which persisted for 5 minutes. The mixture was cooled to $-78°$ and treated with a solution of 16.7 g (50 mmol) of 1-[[4-(1,4-dioxaspiro[4.4]non-7-yl)-2,5 difluorophenyl]carbonyl]-1H-imidazole in 100 ml of dry tetrahydrofuran. The suspension was stirred at $-78°$ for 45 minutes, then allowed to warm to $-35°$ and poured into a mixture of ice, water, and concentrated hydrochloric acid (17.0 ml–0.2 mole). The organic layer was separated, washed with water, 5% sodium bicarbonate, dilute hydrochloric acid, and water. After drying over magnesium sulfate, the solvent was removed in vacuo to give 13.8 g of the title compound.

Example BB 4-(1,4-Dioxaspiro[4.4]non-7-yl)-α-(ethoxymethylene)-2,5-difluoro-β-oxobenzenepropanoic acid, ethyl ester A solution of 35.4 g (0.1 mol) of ethyl 2,5-difluoro-4-(1,4-dioxaspiro[4.4]non-7-yl)-β-oxobenzenepropanoic acid, ethyl ester 22.2 g (0.15 mol) triethyl orthoformate and 150 ml of acetic anhydride was heated at reflux for 4 hours. The solvent was removed in vacuo and the residue was triturated with ethanol and toluene (150 ml ea) which was also removed in vacuo, then high vacuo at 50°. The residue was used without further purification.

Example CC

α-[(Cyclopropylamino)methylene]-4-(1,4-dioxaspiro[4.4]non-7-yl)-2,5-difluoro-β-oxobenzenepropanoic acid, ethyl ester A solution of 20.5 g (50 mmol) of 4-(1,4-dioxaspiro[4.4]non-7-yl)-α-(ethoxymethylene)-2,5-difluoro-β-oxobenzenepropanoic acid, ethyl ester in 200 ml of ethanol was cooled to 10° and treated dropwise with 3.4 g (60 mmol) of cyclopropylamine maintaining the temperature below 15° with an ice bath. After the addition was complete, the reaction was stirred at 5°–15° for 1.5 hours and then at room temperature for 1 hour. The resulting suspension was chilled to 5° and the solid removed by filtration, washed with ethanol, then hexane. The combined filtrate and washings were evaporated in vacuo and the residue was recrystallized from hexane to give 17.5 g of the title compound.

Example DD 3-(4-Bromo-2,5-difluorophenyl)cyclopentylamine hydrochloride

A solution of 20.3 g (50 mmol) of 2-[3-(4-bromo-2,5-difluorophenyl)cyclopentyl]-1H-isoindole-1,3-(2H)-dione in 100 ml of concentrated hydrochloric acid and 100 ml of ethanol was heated at reflux for 4 hours. The ethanol was allowed to evaporate and the aqueous acid mixture was heated at reflux for 4 additional hours. The solution was filtered through a fiber glass pad to remove some insoluble material and the filtrate was evaporated in vacuo. The residue was triturated with ethanol which was also removed in vacuo to give 13.1 g of the title compound.

Example EE

1-[3-(4-Bromo-2,5-difluorophenyl)cyclopentyl]-2,2,5,5-tetramethyl-1-aza-2,5-disilacyclopentane A suspension of 15.7 g (50 mmol) of 3-(4-bromo-2,5-difluorophenyl)cyclopentylamine hydrochloride in 250 ml of dry methylene chloride was treated with 15.2 g (0.15 mol) of triethylamine under an argon atmosphere. To this was added a solution of 11.25 g (50 mmol) of 1,1,4,4-tetramethyl-1,4-dichlorosilylethylene in 25 ml of dry methylene chloride. The mixture was stirred at room temperature for 4 hours and filtered through a fiber glass pad. The solvent was removed in vacuo, the residue triturated with 100 ml of petroleum ether, and the solid was removed by filtration. The filtrate was evaporated in vacuo to give 20 g of the title compound which was used without further purification.

Example FF

4-[3-(Amino)cyclopentyl]-2,5-difluorobenzoic acid hydrochloride

A solution of 21.0 g (50 mmol) of 1-[3-(4-bromo-2,5-difluorophenyl)cyclopentyl]-2,2,5,5-tetramethyl-1-aza-2,5disilacyclopentane in 200 ml of dry tetrahydrofuran, under an argon atmosphere, was treated with 20 ml (50 mmol) of 2.5 M n-butyl lithium in hexane. The solution was warmed to −40° and poured onto 300 g of finely crushed dry ice and the mixture allowed to stand until the dry ice evaporated. The solution was treated with 100 ml of 1.0 M hydrochloric acid, stirred at room temperature for 1 hour, and evaporated in vacuo. The residue was triturated with toluene which was also evaporated in vacuo to give 10.6 g of the title compound.

Example 1

Ethyl 1-cyclopropyl-6-fluoro-1,4-dihydro-7-(1-methyl-4-piperidinyl)-4-oxo-3-quinolinecarboxylate A solution of 3.91 g (10 mmoles) of ethyl α-[(cyclopropylamino)methylene]-2,5-difluoro-4-(1-methyl-4-piperidinyl)-β-oxobenzenepropanoate in 50 ml of t-butyl alcohol was treated with 1.23 g (11 mmoles) of potassium t-butoxide and heated at 65° C. for 1½ hours. The mixture was evaporated under vacuum and the residue was stirred in 50 ml of water and neutralized with 1 N HCl. After extraction with chloroform the organic layer was dried (MgSO₄) and evaporated to afford the title compound.

Example 2

1-Cyclopropyl-6-fluoro-1,4-dihydro-7-(1-methyl-4-piperidinyl)-4-oxo-3-quinolinecarboxylic acid hydrochloride A solution of 3.71 g (10 mmoles) of ethyl 1-cyclopropyl-6-fluoro-1,4-dihydro-7-(1-methyl-4-piperidinyl)-4-oxo-3-quinolinecarboxylate in 50 ml 6 N HCl was refluxed 1 hour and evaporated to dryness to afford the title compound.

Example 3

7-[3-(Acetylamino)cyclopentyl]-1-cyclopropyl-6-fluoro-1,4-dihydro-4-oxoquinoline-3-carboxylic acid, ethyl ester A solution of 21.0 g (50 mmol) of 4-[3-(acetylamino)cyclopentyl]-α-[(cyclopropylamino)methylene]-2,5-difluoro-β-oxobenzenepropanoic acid, ethyl ester in 250 ml of dry t-butanol was treated with a slurry of 6.2 g (55 mmol) of potassium t-butoxide in 50 ml of dry t-butanol. The resulting suspension was stirred and heated at 65° for 3 hours and then at room temperature overnight. The solvent was removed in vacuo and the residue was dissolved in methylene chloride and washed with 1.0 M hydrochloric acid. After drying (MgSO₄) and evaporating the solvent in vacuo, the residue was recrystallized from ethyl acetate/hexane to give 16.5 g of the title compound.

Example 4

7-[3-(Amino)cyclopentyl]-1-cyclopropyl-6-fluoro-1,4-dihydro-4-oxoquinoline-3-carboxylic acid hydrochloride A mixture of 20.0 g (50 mmol) of 7-[3-(acetylamino)-cyclopentyl]-1-cyclopropyl-6-fluoro-1,4-dihydro-4-oxoquinoline-3-carboxylic acid, ethyl ester was heated in a mixture of 6.0 M hydrochloric acid/ethanol (20 ml/150 ml) at reflux for 8 hours. The solvent was removed in vacuo and the residue slurried in 200 ml of water and filtered. The filtrate was evaporated in vacuo and the residue triturated in ethanol and filtered. The precipitate was washed with ethanol, ether, and dried in vacuo to give 13.6 g of the title compound.

Example 5

7-(1,4-Dioxaspiro[4.4]non-7-yl)-1-cyclopropyl-6-fluoro-1,4-dihydro-4-oxoquinoline-3-carboxylic acid, ethyl ester A solution of 21.4 g (50 mmol) of α-[(cyclopropylamino) methylene]-4-(1,4-dioxaspiro[4.4]non-7-yl)-2,5-difluoro-β-oxobenzenepropanoic acid, ethyl ester in 250 ml of dry t-butanol was treated with a slurry of 6.2 g (55 mmol) of potassium t-butoxide in 150 ml of dry t-butanol. The resulting suspension was stirred at 65° for 4 hours and then at room temperature overnight. The solvent was removed in vacuo and the residue was dissolved in methylene chloride and washed with 1.0 M hydrochloric acid. After drying (MgSO₄) and evaporating the solvent in vacuo, the residue was recrystallized from ethyl acetate/hexane to give 17.3 g of the title compound.

Example 6

7-(3-Oxocyclopentyl)-1-cyclopropyl-6-fluoro-1,4-dihydro-4-oxoquinoline-3-carboxylic acid A solution of 20 g (50 mmol) of 7-(1,4dioxaspiro[4.4]-non-7-yl)-1-cyclopropyl-6-fluoro-1,4-dihydro-4-oxoquinoline-3-carboxylic acid, ethyl ester in 150 ml of ethanol and 100 ml of 6.0 M hydrochloric acid was heated at reflux for 6 hours. The solvent was removed in vacuo to give 31.6 g of the title compound.

Example 7

7-[(3-Oximino)cyclopentyl]-1-cyclopropyl-6-fluoro-1,4-dihydro-4-oxoquinoline-3-carboxylic acid A solution of 3.8 g (55 mol) of hydroxylamine hydrochloride in 100 ml of water was neutralized by the addition of 55 ml (55 mmol) of 1.0 N sodium hydroxide. To this was added a suspension of 16.5 g (50 mmol) of 7-(3 oxocyclopentyl)-1-cyclopropyl-6-fluoro-1,4-dihydro-4-oxoquinoline acid in a mixture of 150 ml of ethanol and 50 ml (50 mmol) of 1.0 N sodium hydroxide. The reaction mixture was heated at 60° for 4 hours and then at room temperature overnight. The alcohol was removed in vacuo and the aqueous was acidified to pH 2.0 with 6.0 M hydrochloric acid. The solid was removed by filtration, washed with water, and dried in vacuo to give 16.1 g of the title compound.

Example 8

7-[3-(Amino)cyclopentyl]-1-cyclopropyl-6-fluoro-1,4-dihydro-4-oxoquinoline-3-carboxylic acid hydrochloride A suspension of 17.2 g (50 mmol) of 7-[(3oximino)cyclopentyl]-1-cyclopropyl-6-fluoro-1,4-dihydro-4-oxoquinoline-3-carboxylic acid, 3.0 g of Raney-nickel and 300 ml of N,N-dimethylformamide was shaken in a hydrogen atmosphere at 45-50 psi for 24 hours. After removing the catalyst by filtration through Celite and addition of 100 ml of 6.0 M hydrochloric acid (60 mmol), the mixture was evaporated in high vacuo at 50°. The residue was triturated with a mixture of 200 ml of ethanol/ether (1:1) and the solid was removed by filtration, washed with ethanol/ether (1:1) and dried in vacuo to give 13.1 g of the title compound.

Example 9

1-Cyclopropyl-6-fluoro-1,4-dihydro-4-oxo-7-(4-piperidinyl)-3-quinolinecarboxylic acid A solution of 0.51 g (1.28 mmol) ethyl 7-(1-acetyl-4-piperidinyl)-1-cyclopropyl-6-fluoro-1,4-dihydro-4-oxo-3quinolinecarboxylate in 12 ml of methanol and 2 ml of 2 N sodium hydroxide was refluxed 114 hours. The mixture was evaporated under vacuum and the residue was redissolved in water. Titration with dilute hydrochloric acid to pH 7 afforded the title compound as a solid which was filtered and dried, mp 292°-293° C. (decomp.)

Example 10

Ethyl 7-(1-acetyl-4-piperidinyl)-1-cyclopropyl-6-fluoro-1,4-dihydro-4-oxo-3-quinolinecarboxylate A solution of 3.49 g (8.30 mmol) ethyl 4-(1-acetyl-4-piperidinyl)-α-[(cyclopropylamino)methylene]-2,5-difluoro-β-oxobenzenepropionate in 35 ml of t-butyl alcohol was treated with 0.93 g (8.30 mmol) potassium t-butoxide and stirred in an oil bath at 65° for 1.5 hours. The mixture was evaporated under vacuum and the residue extracted with 0.5 N hydrochloric acid. The organic layer was dried (MgSO₄) and evaporated. The title compound was isolated by chromatography on silica gel and crystallization from toluene, mp 195°-201° C.

Intermediates for Example 10

Ethyl 4-(1-acetyl-4-piperidinyl-α-[(cyclopropylamino)methylene]-2,5-difluoro-β-oxobenzenepropionate A solution of 3.30 g (8.05 mmol) of ethyl 4-(1-acetyl-4-piperidinyl)-α-(ethoxymethylene)-2,5-difluoro-β-oxobenzenepropionate in 40 ml of ethyl ether was treated with 10 0.55 g of cyclopropylamine and stirred at room temperature for 6 hours. The title compound was isolated as a syrup after evaporating under vacuum.

Ethyl 4-(1-acetyl-4-piperidinyl)-α-(ethoxymethylene)-2,5-difluoro-β-oxobenzenepropionate A solution of 2.68 g (7.57 mmol) ethyl 4-(1-acetyl-4-piperidinyl)-2,5-difluoro-β-oxobenzenepropionate in 16 ml of acetic anhydride and 1.9 ml of triethyl orthoformate was refluxed 1.25 hours. The title compound was isolated as a syrup after evaporation under vacuum in an oil bath at 80° C.

Ethyl 4-(1-acetyl-4-piperidinyl)-2,5-difluoro-β-oxobenzenepropionate

A solution of 2.25 g (7.95 mmol) 1-acetyl-4-(4-carboxy-2,5-difluorophenyl)-piperidine in 120 ml of dry tetrahydrofuran at 0° C. was treated with 2.00 g (12.3 mmol) carbonyldiimidazole. The mixture was let warm to room temperature, stirred 1.5 hours, and treated with 3.10 g (10.8 mmol) of magnesium ethyl malonate. The mixture was stirred overnight, refluxed 1.5 hours, evaporated to dryness and shaken with a mixture of ethyl acetate and 3 N hydrochloric acid. The organic layer was washed with sodium bicarbonate solution, dried (MgSO$_4$) and evaporated to afford the title compound as a syrup.

1-Acetyl-4-(4-carboxy-2,5-difluorophenyl)-piperidine

A solution of 0.84 g (3 mmol) of 1-acetyl-4-(4-carboxy-2,5-difluorophenyl)-1,2,3,6-tetrahydropyridine in 250 ml of acetic acid with 0.5 g of 10% Pd/c catalyst was hydrogenated at 50 psi. The title compound was isolated after filtration of the catalyst, evaporation and crystallization from acetic acid-water, mp 206°–207° C.

4-(4-Carboxy-2,5-difluorphenyl)-1-acetyl-1,2,3,6-tetrahydropyridine

A suspension of 8.51 g (29.1 mmol) 4-(4-carboxy-2,5-difluorophenyl)-1,2,3,6-tetrahydropyridine hydrochloride in 90 ml acetic anhydride was stirred at reflux for 0.75 hour. The resulting solution was evaporated to dryness and the residue stirred with water, filtered, and crystallized from acetic acid-water to afford the title compound, mp 241°–242° C.

4-(4-Carboxy-2,5-difluorophenyl)-1,2,3,6-tetrahydropyridine hydrochloride

A suspension of 10.00 g (34.25 mmol) of 4-(4-cyano-2,5-difluorophenyl)-1-ethoxycarbonyl-1,2,3,6-tetrahydropyridine in 350 ml of 6 N hydrochloric acid was stirred at reflux for 23 hours. The resulting solution was evaporated to dryness and the residue crystallized from water to give the title compound, mp 286°–290° C. (decomp.).

4-(4-Cyano-2,5-difluorophenyl)-1-ethoxycarbonyl-1,2,3,6-tetrahydropyridine

A mixture of 27.60 g (79.8 mmol) 1-ethoxycarbonyl-4-(4-bromo-2,5-difluorophenyl)-1,2,3,6-tetrahydropyridine and 9.00 g (89.6 mmol) cuprous cyanide in 300 ml N,N-dimethylformamide was stirred at reflux for 20 hours. The mixture was cooled and shaken with 800 ml concentrated ammonium hydroxide, 800 ml water and 1,000 ml of dichloromethane. The organic layer was washed with water, dried (MgSO$_4$) and evaporated. The product was purified by chromatography on silica gel and crystallization from hexane to give the title compound, mp 85°–87° C.

4-(4-Bromo-2,5-difluorophenyl)-1-ethoxycarbonyl-1,2,3,6-tetrahydropyridine

A solution of 11.12 g (30.5 mmol) 4-(4-bromo-2,5-difluorophenyl)-1-ethoxycarbonyl-4-piperidinol and 0.70 g of p-toluenesulfonic acid in 200 ml toluene was refluxed with a Dean-Stark trap for 16 hours. The mixture was cooled, extracted with sodium bicarbonate solution, dried (MgSO$_4$), evaporated and the residue flash chromatographed on a column of silica gel to afford a syrup which crystallized on standing, mp 40°–44° C.

4-(4-Bromo-2,5-difluorophenyl)-1-ethoxycarbonyl-4-piperidinol

A solution of 16.55 g (60.85 mmol) 1,4-dibromo-2,5-difluorobenzene in 400 ml of ethyl ether stirred at −75° C. under an argon atmosphere was treated dropwise with 24.3 ml of 2.5 M n-butyl lithium in hexane. The mixture was let warm to −50° C. and treated dropwise with a solution of 11.00 g (64.33 mmol) 1-ethoxycarbonyl-4-piperidone in 100 ml ethyl ether. After stirring a further 0.25 hour, the mixture was let warm to room temperature and extracted with ammonium chloride solution. The organic layer was dried (MgSO$_4$), evaporated and the crude product chromatographed on a silica gel column and crystallized from toluene hexane to afford the title compound, mp 133°–136° C.

Example 11

1-Cyclopropyl-6-fluoro-1,4-dihydro-4-oxo-7-(1,2,3,6-tetrahydro-4-pyridyl)-3-cuinolinecarboxylic acid A solution of 0.80 g (2.01 mmol) of ethyl 7-(1-acetyl-1,2,3,6-tetrahydro-4-pyridyl)-1-cyclopropyl-6-fluoro-1,4-dihydro-4-oxo-3-quinolinecarboxylate in 50 ml of 6 N hydrochloric acid was heated on a steam bath for 2.75 hours. The mixture was evaporated to dryness, redissolved in water, filtered and titrated to pH 7 with dilute sodium hydroxide. The precipitated title compound was filtered and dried.

Intermediate for Example 11

Ethyl 7-(1-acetyl-1,2,3,6-tetrahydro-4-pyridyl)-1-cyclopropyl-6-fluoro-1,4-dihydro-4-oxo-3-quinolinecarboxylate A solution of 4.70 g (11.3 mmol) of ethyl 4-(1-acetyl-1,2,3,6-tetrahydro-4-pyridyl)-α-[(cyclopropylamino)methylene]-2,5-difluoro-β-oxobenzenepropionate in 35 ml of t-butyl alcohol was treated with 1.26 g (11.3 mmol) potassium t-butoxide and stirred in an oil bath at 65° C. for 5.5 hours. The mixture was evaporated under vacuum and the residue was dissolved in chloroform and extracted with 0.5 N hydrochloric acid. The organic layer was dried (MgSO$_4$), evaporated and the title compound purified by chromatograph on silica gel and crystallization from toluene, mp 190°–192° C.

Ethyl 4-(1-acetyl-1,2,3,6 TM tetrahydro-4-pyridyl)-α-[(cyclopropylamino)methylene]-2,5-difluoro-β-oxobenzenepropionate A solution of 4.50 g (11.06 mmol) of ethyl 4-(1-acetyl-1,2,3,6-tetrahydro-4-pyridyl)-α-(ethoxymethylene)-2,5-difluoro-β-oxobenzenepropionate in 50 ml of ethyl ether was treated with 0.77 g (13.5 mmol) of cyclopropylamine and stirred for 22 hours. The title compound was isolated as a syrup after evaporation under vacuum.

Ethyl 4-(1-acetyl-1,2,3,6-tetrahydro-4-pyridyl)-α-(ethoxymethylene)-2,5-difluoro-β-oxobenzenepropionate A solution of 3.95 g (11.25 mmol) ethyl 4-(1-acetyl-1,2,3,6-tetrahydro-4-pyridyl)-2,5-difluoro-β-oxobenzenepropionate in 25 ml of acetic anhydride and 2.8 ml of trietyl orthoformate was refluxed 1.5 hours. The title compound was isolated as a syrup after evaporation under vacuum in an oil bath at 80° C.

Ethyl 4-(1-acetyl-1,2,3,6-tetrahydro-4-pyridyl)-2,5-difluoro-β-oxobenzenepropionate.

A solution of 3.00 g (10.7 mmol) of 1-acetyl-4-(4-carboxy-2,5-difluorophenyl)-1,2,3,6-tetrahydropyridine in 160 ml of dry tetrahydrofuran at 0° C. was treated with 2.67 g (16.4 mmol) of carbonyldiimidazole. The mixture was stirred 2.5 hours at room temperature, treated with 4.13 g (14.4 mmol) magnesium ethyl malonate, stirred overnight, refluxed 2 hours, evaporated and shaken with a mixture of ethyl acetate and 3 N hydrochloric acid. The organic layer was extracted with sodium bicarbonate solution, dried and evaporated to give the title compound as a syrup.

We claim:
1. A compound named 4-(4-bromo-2,5-difluorophenyl)-1-methyl-4-piperidinol.
2. A compound named 4-(4-bromo-2,5-difluorophenyl)-1,2,3,6-tetrahydro-1-methylpyridine.
3. A compound named 2,5-difluoro-4-(1-methyl-4-hydroxy-4-piperidinyl)benzoic acid.
4. A compound named 2,5-difluoro-4-(1-methyl-4-piperidinyl)benzoic acid.
5. A compound named 2,5-difluoro-4-(1-methyl-4-piperidinyl)-β-oxobenzenepropanoate.
6. A compound named α-(ethoxymethylene)-2,5-difluoro-4-(1-methyl-4-piperidinyl)-β-oxobenzenepropanoate.
7. A compound named ethyl α-[(cyclopropylamino)methylene]-2,5-difluoro-4-(1-methyl-4-piperidinyl)-β-oxobenzenepropanoate.

* * * * *